United States Patent [19]

Lavin

[11] Patent Number: 4,668,192

[45] Date of Patent: May 26, 1987

[54] APPARATUS AND METHOD FOR EXECUTING ORTHODONTIC PROCEDURE

[76] Inventor: Joseph J. Lavin, W. 508 - 7th, Spokane, Wash. 99204

[21] Appl. No.: 562,228

[22] Filed: Dec. 16, 1983

[51] Int. Cl.$^4$ ............................................. A61C 13/08
[52] U.S. Cl. .................................. 433/205; 433/210; 433/74
[58] Field of Search .............................. 433/202–213, 433/171–175, 167, 74, 56, 2, 169, 220, 221

[56] References Cited

U.S. PATENT DOCUMENTS

| | | | |
|---|---|---|---|
| 1,109,651 | 9/1914 | Merker | 433/210 |
| 2,854,746 | 10/1958 | Lester et al. | 433/169 |
| 2,857,670 | 10/1958 | Kiernan, Jr. | 433/175 |
| 2,880,508 | 4/1959 | Lester et al. | 433/205 |
| 3,226,827 | 1/1966 | Spalten | 433/74 |
| 3,439,421 | 1/1967 | Perkowski | 433/24 |
| 3,521,354 | 8/1968 | Stern et al. | 433/74 |
| 3,521,355 | 7/1970 | Pearlman | 433/3 |
| 3,557,817 | 4/1972 | Kesling | 433/14 |
| 3,896,548 | 7/1975 | Zahn | 433/74 |
| 4,238,189 | 12/1980 | Tirino | 433/74 |
| 4,521,188 | 6/1985 | Metzler | 433/74 |

Primary Examiner—John J. Wilson
Assistant Examiner—J. Hakomaki
Attorney, Agent, or Firm—Wells, St. John & Roberts

[57] ABSTRACT

The present invention is provided to render quality orthodontic treatment, with proper dispersion of the patient's teeth roots in the supporting medium. The present system involves procedure which establishes and records the location of the patient's individual tooth roots to the visual crowns of the associated teeth. This is accomplished by use of simulated root structures that are attachable to individual crown models of the patient's teeth and oriented in relation to the models such that the axes of the associated roots are made accessible. The individual simulated root structures may be attached to crown models taken from a direct impression from the patient's mouth. The individual crown models are aligned in a surveyor mechanism and attached with their long axes in coaxial alignment with the central axes of dop rods. The dop rods are then held on a grinding rack and moved toward a flat grinding surface which produces a plane flat surface on each crown model. The stimulated roots may then be attached via a mounting arrangement such that root fins of the simulated roots directly indicate the orientation of the actual tooth roots. The finished tooth model assemblies, including the crown models and attached simulated roots can then be repositioned in the original impression and poured to form a mal-occlusion model. This model, with simulated roots exposed, indicates the exact orientation of individual tooth roots surrounded by the adjacent gum tissue. The crown models can be separated from the model and re-assembled with new simulated roots to be positioned in a set-up articulator into an ideal arch form, representing the corrected positions of the teeth. The finished tooth models, while in their ideal "setup" can again be poured up to form an ideal set-up model. This model is used to indicate the orientation of the individual tooth roots as they may exist in the final corrected positions within the patient's mouth. The ideal set-up model can be used with a bracket slot orienting and placement instrument for appropriate selection and placement of arch wire brackets on the individual tooth models. Appropriate mechanisms are provided to indicate bracket thickness and backing curvature so the precision slots of the selected brackets will be precisely oriented on each crown model. Selected brackets can then be placed on the individual tooth models which are then moved from the ideal set-up and returned to the simulated root sections left in the original mal-occlusion cast model. The brackets are then positioned precisely as they should be in the patient's mouth.

18 Claims, 39 Drawing Figures

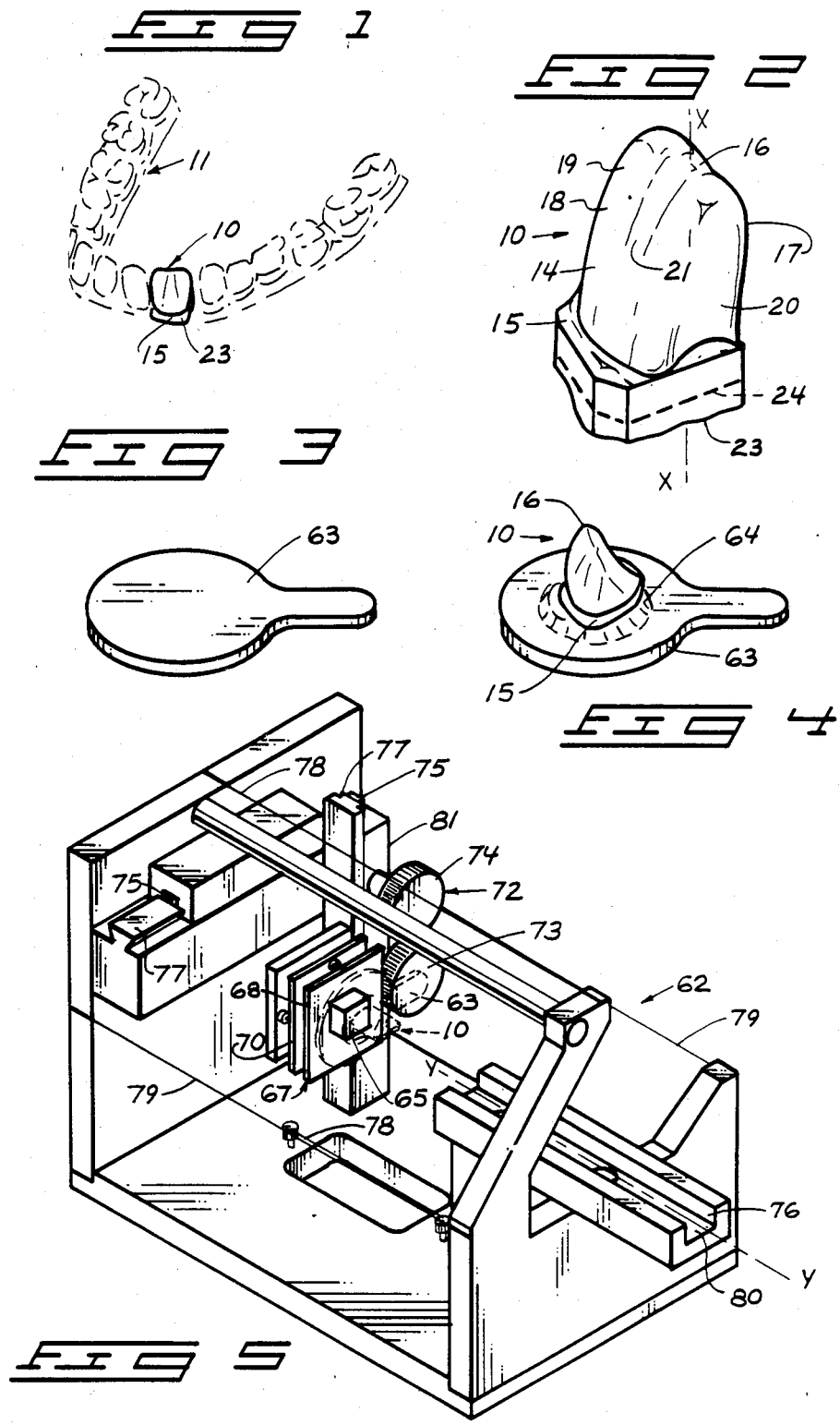

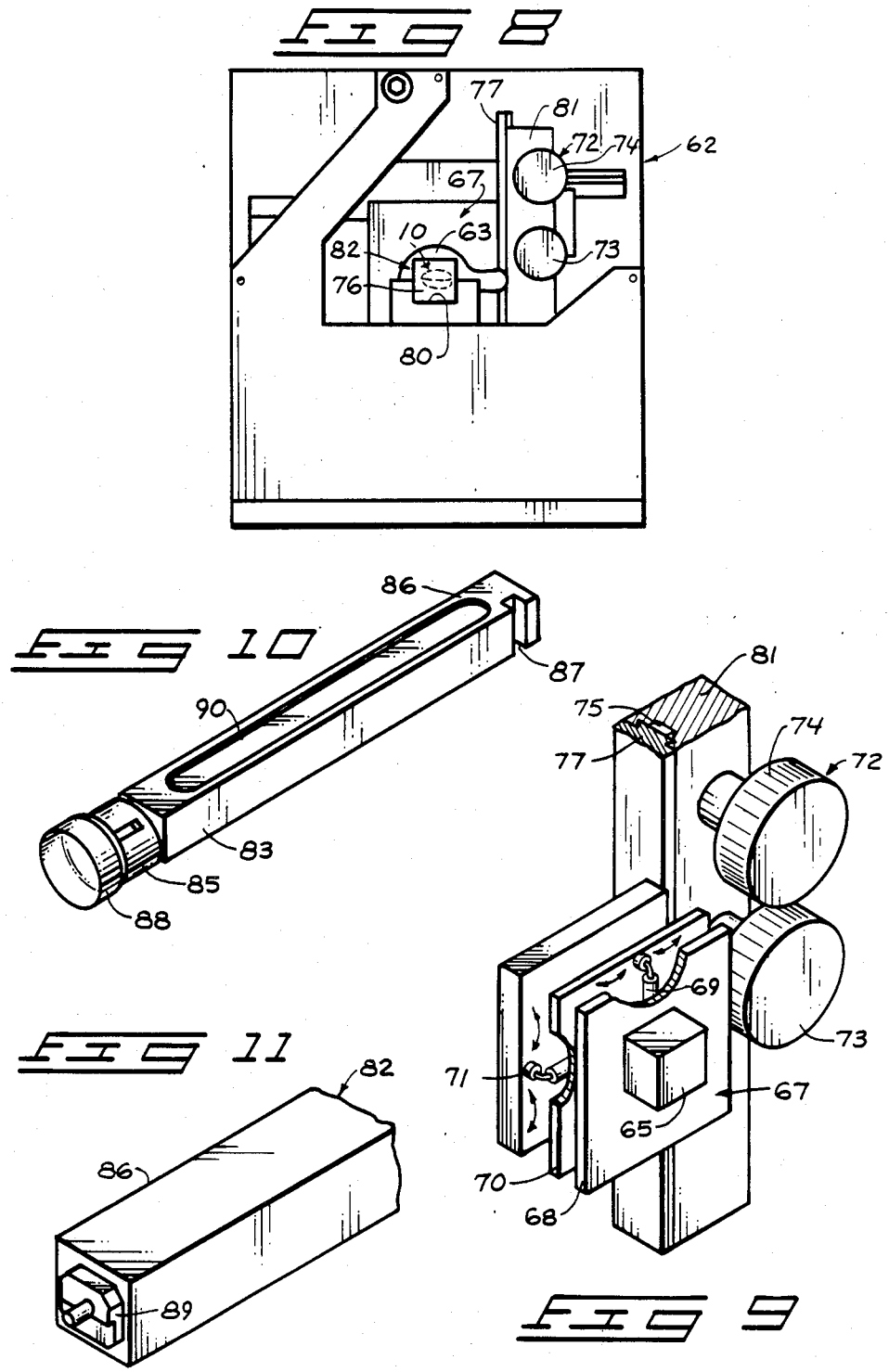

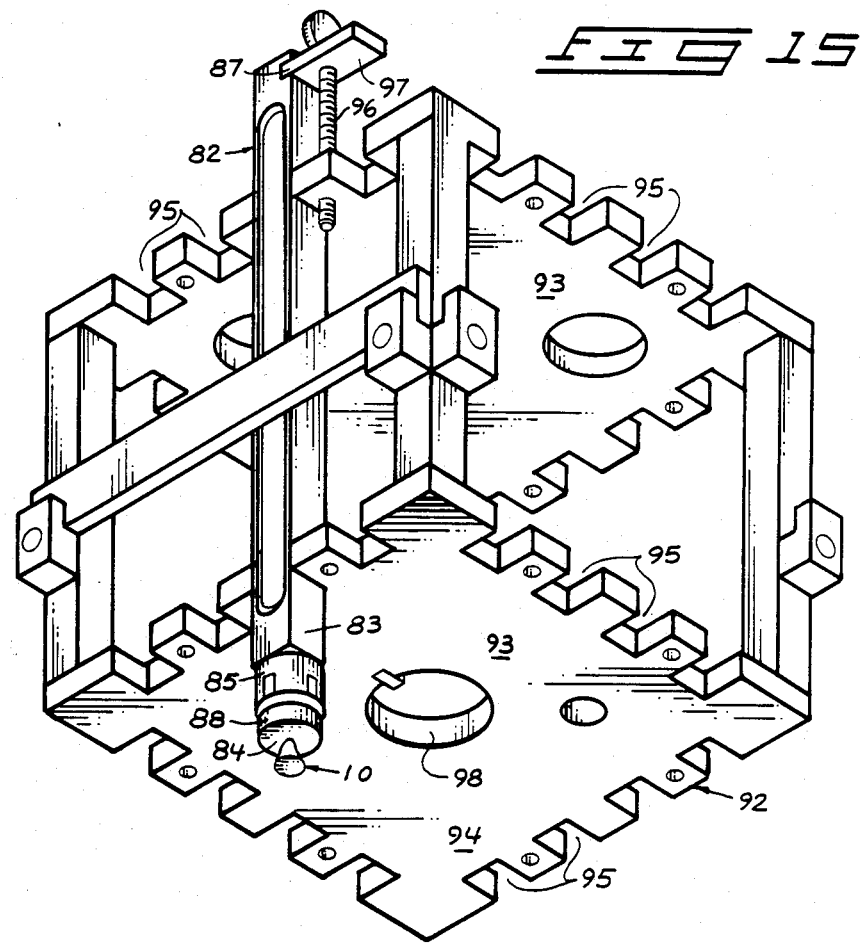
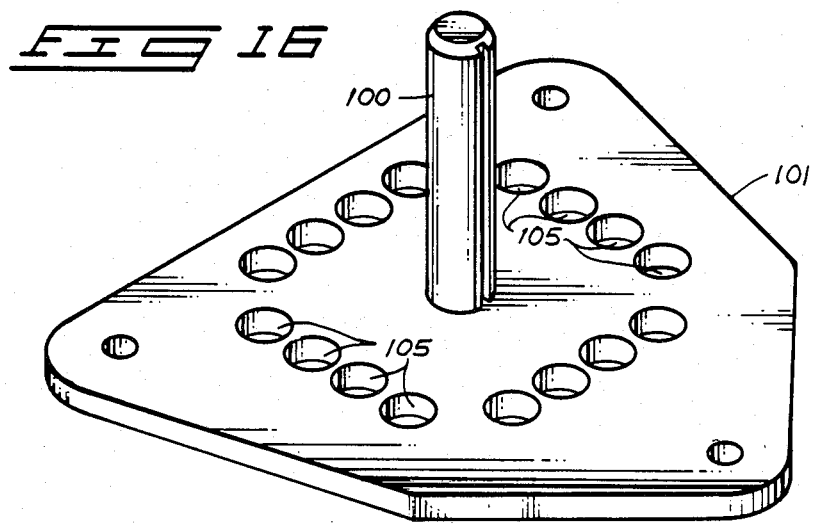

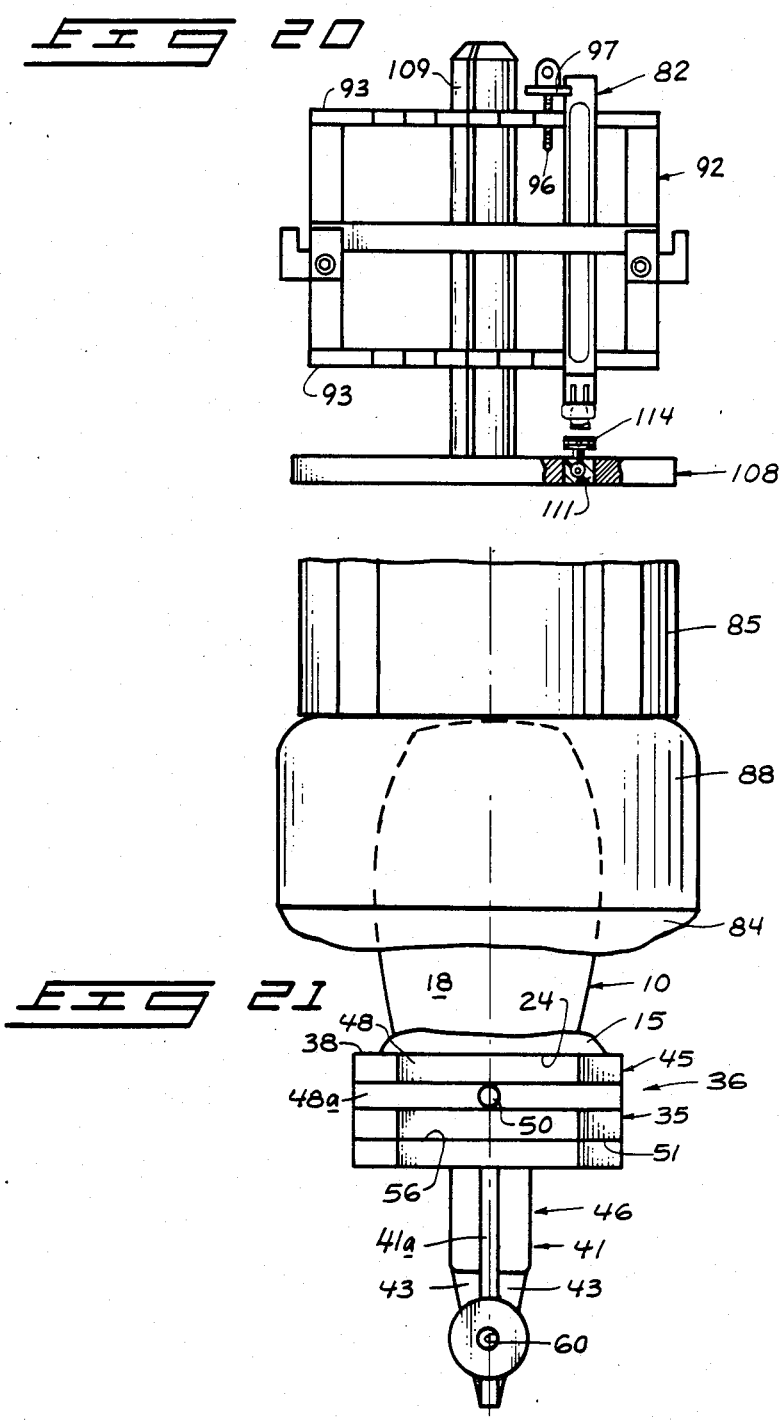

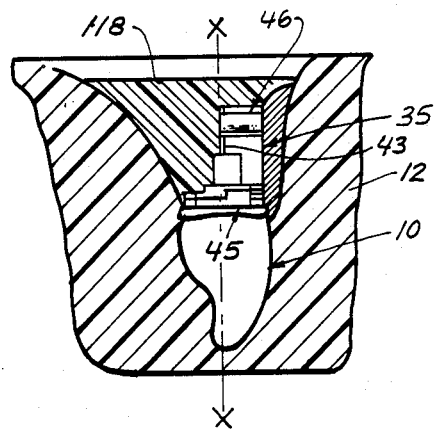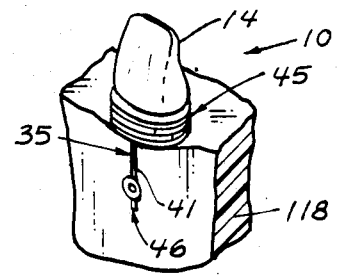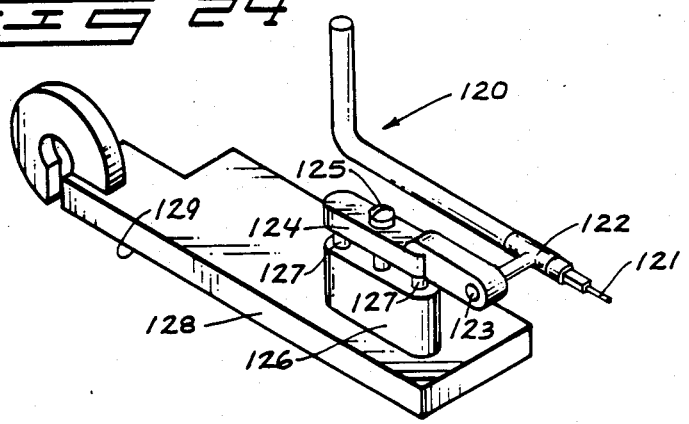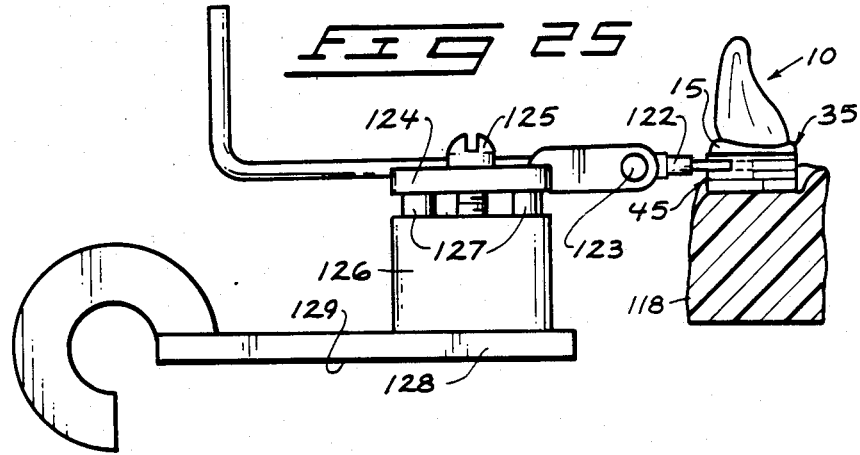

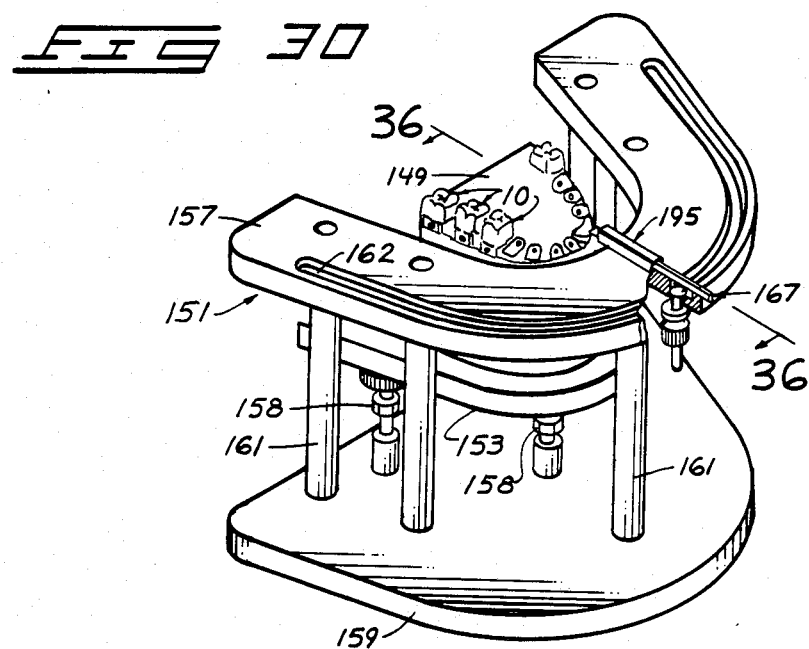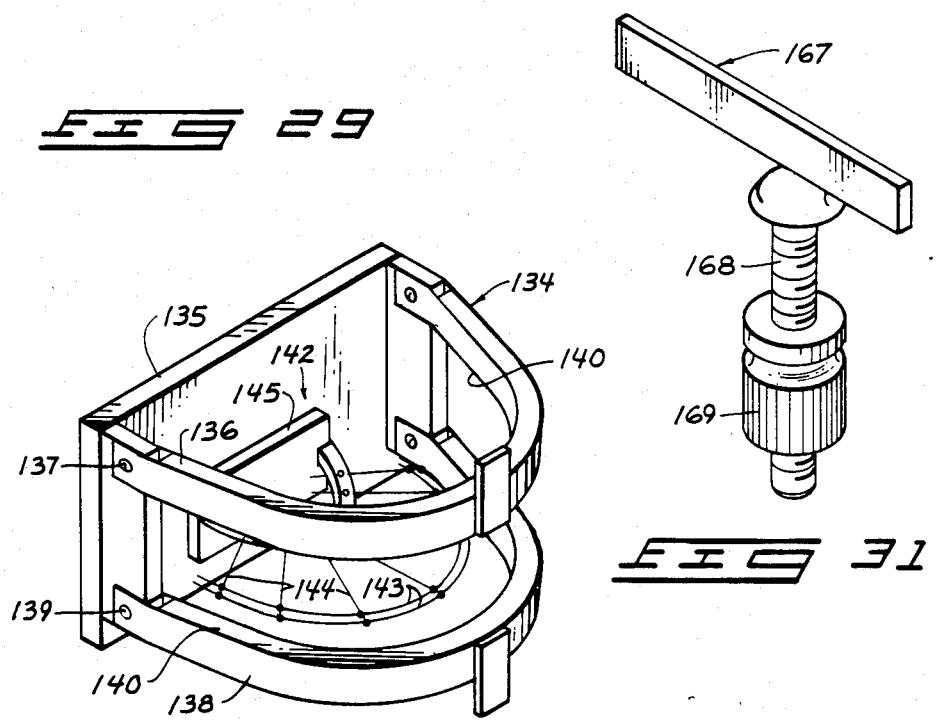

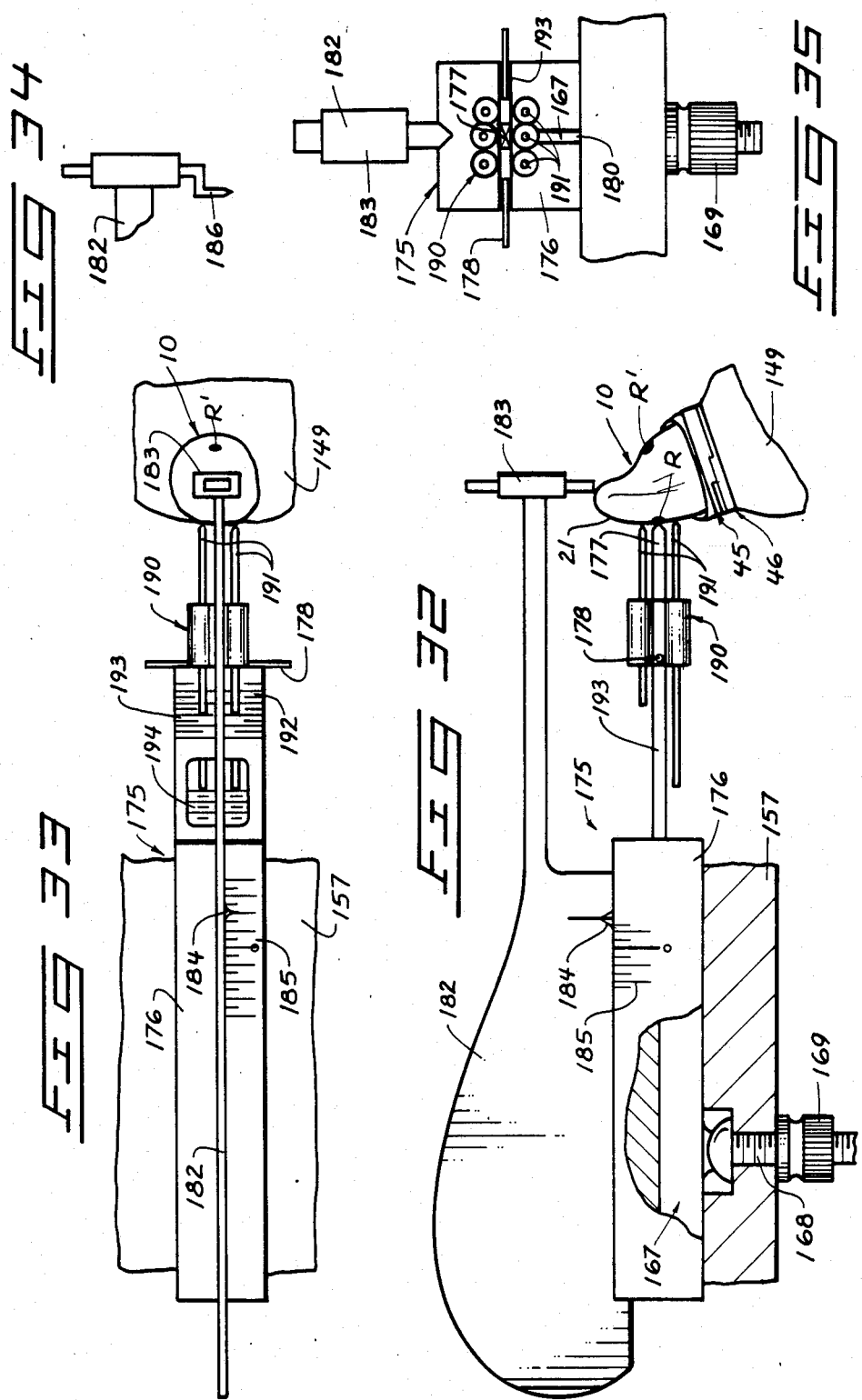

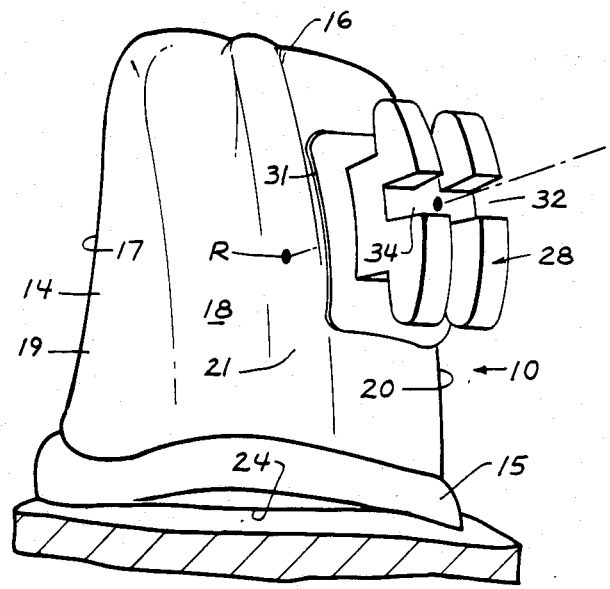
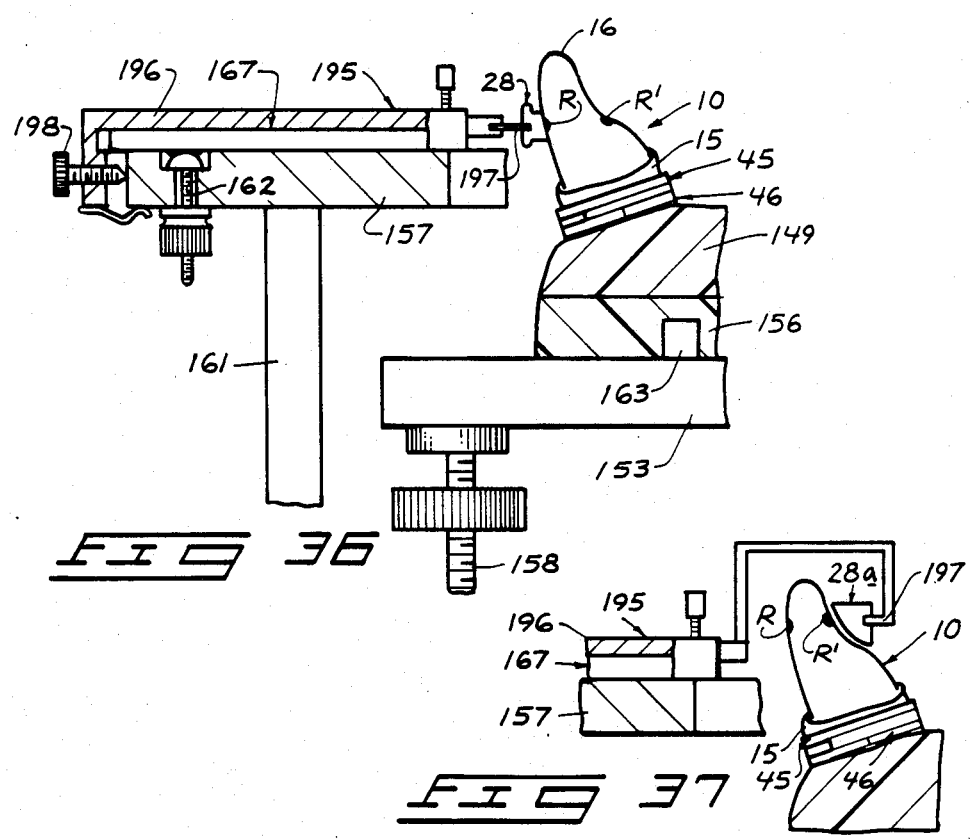

APPARATUS AND METHOD FOR EXECUTING ORTHODONTIC PROCEDURE

FIELD OF THE INVENTION

The present invention relates broadly to the field of orthodontic treatment of human teeth and more particularly to an apparatus system and process for locating and recording in a readily retrievable manner the spatial information regarding specific crown-to-root relationships of individual teeth and in using such information to facilitate orthodontic diagnosis and treatment planning, proper orthodontic bracket placement and force system design, evaluation of the force systems employed and treatment progress.

BACKGROUND OF THE INVENTION

Orthodontists are principally concerned with the straightening of irregular or "mal-occluded" teeth. Generally the corrective technique first involves diagnosing the extent of the mal-occlusion and devising a course of treatment in which teeth are repositioned into a desired configuration. The desired configuration of the teeth in the dental arches, traditionally, has had the following characteristics:

1. The occlusal (biting) surfaces of the crowns of the teeth in the upper and lower dental arches meet in a relatively flat "occlusal" plane; and
2. The cusps of the crowns in one arch interdigitate with the cusps of the crowns of the opposing arch in a prescribed manner.

In recent years the position of the tooth roots in the bone has become an important added characteristic of the desired configuration of the teeth at the completion of orthodontic treatment. This characteristic is stated as "proper dispersion of the roots in the supporting medium (bone)".

To obtain these characteristics of the desired configuration of the dental arches and in particular, "the proper dispersion of the roots in the supporting medium", certain information is essential. Further, the accuracy of this information can improve the level of treatment.

The knowledge of the root position of each tooth which is buried in the supporting bone is of paramount importance for orthodontic treatment from early diagnosis of the mal-occlusion and throughout the treatment period to its conclusion.

Thus, if the orthodontist knows the precise position of the roots, he or she is able to:

(a) better assess the mal-occlusion;
(b) formulate a treatment plan including proper root dispersion;
(c) orient the precision slot of an orthodontic bracket to the crown and root of each tooth;
(d) design proper force systems (moment to force ratio) to control movement of the tooth roots as well as the crowns; and
(e) evaluate the efficiency of the force systems and assess crown and root movement throughout the orthodontic treatment period.

Once the diagnosis and treatment plan has been formulated, the orthodontist attaches orthodontic brackets (braces) on the crowns of the patient's teeth. The accuracy of properly orthodontic bracket placement on the crowns of the teeth is considered by the orthodontist as the most important procedure in all of treatment. This is because the orthodontic bracket which is usually made of metal, has a precision slot that must be oriented properly to the long axis of the tooth. This precision slot is some 2–4 mm in length and rectangular in cross-section to receive an "arch wire". An arch wire is a length of springy, small diameter wire that the orthodontist shapes around the dental arch from crown to crown to be received by the precision slot of each bracket on the crown of each tooth.

Initially small diameter arch wires are placed—wires that fit loosely in the precision bracket slots. As the bracket slots begin to line up, one to another, larger diameter arch wires can be placed. Ideally, a full size arch wire (one whose cross-section totally fills the precision bracket slot) can eventually be placed in all the bracket slots for all the teeth in one arch. Because the precision slot of the bracket and the larger arch wire are the same size and rectangular shape in cross section, the arch wire can control the bracket in all planes of space.

The bracket is attached to the crown of the tooth and each crown has an attached root, thus the arch wire controls the crown and root of each tooth in all planes of space. The relationship of the attachment of the crown to the root is constant and is not altered during orthodontic treatment.

Therefore, if the slot of each bracket could be oriented properly to the crown and root of each tooth and so attached to the crown of each tooth, a full size flat rectangular arch wire placed in each bracket slot would properly position all the crowns in relation to each other and, in addition, would properly disperse all the roots.

Generally, one of two methods is used to place brackets on the patient's teeth to accept the spring arch wires. These are the direct and the indirect methods.

The direct method involves fixing of the arch wire brackets to the teeth directly in the patient's mouth. The orthodontist attempts to center the bracket in a mesial-distal direction plus orient the precision slot to the crown's long axis. The crowns of teeth in a mal-occlusion are in disarray and thus it is frustrating for the orthodontist who must guess at proper bracket placement while controlling lips, tongue and saliva of the patient.

This must be done without accurate knowledge of the crown to root orientation. Further, in the direct method this must be accomplished by visual observation and hand manipulation and inaccuracy of bracket placement is a reality. Inaccurately placed brackets create difficulties in properly adapting arch wires and calculating the force requirements for correcting mal-aligned teeth. In addition, the precision slot of the bracket will not indicate to the orthodontist the position of the tooth root in the surrounding bone. This makes it even more difficult for the orthodontist to analyze and plan a course of corrective development through a period of time.

The indirect method involves initial bracket placement away from the patient in a laboratory atmosphere. In its most rudimentary form, the indirect method involves the same bracket placement procedures used in the direct method with the only difference being that the brackets are first attached to a cast model of the mal-occlusion. They are then removed from the model and placed on the patient's teeth. This process has proven to be more effective than the direct method but is not at all without its own unique difficulties.

To solve some of these difficulties of the indirect method an ideal "set-up" can be done: A "set-up" is a procedure where the individual crowns plus 4–5 mm of the gum tissue area below each crown is cut free of the base of the mal-occlusion cast. Thus, each tooth model consists of a tooth crown and a long section of the gum area directly below the tooth.

The individual tooth models may then be reassembled on a wax rim shaped like a dental arch in an "ideal" arch configuration. To make any change of a tooth position, a spatula is heated and then inserted into the wax around the tooth to be altered. This procedure is tedious, lacks precision in altering tooth positions and, even more importantly, no root structure can ever be evaluated as a part of the set-up method. Only the crowns and some of the gingival (gum) tissue is available for observation. Thus the orthodontist or technician must guess at the long tooth axis to determine proper tooth alignment in the "ideal" set-up. The resulting "ideal" set-up is therefore far from "ideal". It is often an unrealistic, unobtainable set-up because the changes of root angles from the mal-occlusion to the set-up are not coordinated as orthodontically feasible.

Previous indirect methods have made use of the wax base to hold the tooth crown models from the gingival areas of the tooth models while the orthodontist or lab person tries to position the crown. This method of holding the crown obstructs the area where the root of the tooth is actually located. This adds even further difficulty in accomplishing proper dispersion of the tooth root when the area of the roots are not visible.

In the natural dentition, the joint transition section between the crown of a tooth and its root is not visible. The transition sections are imbedded in alveolar bone (bone that forms the socket for the root of a tooth). In addition, a portion of the crown of a tooth and the alveolar bond around the root is covered by various thicknesses of gum tissues.

The closest observation of the transition section between the crown and the root in nature is produced by X-ray. Because an X-ray takes a three dimensional object and reproduces it in two dimensions, accuracy is greatly diminished. This is especially true in mal-occlusions where the third dimension (depth) may be very irregular. Some dimensional input can be obtained, however, by making use of a number of X-rays taken at different recorded angles. However, this is not a practical approach nor is extensive radiation of the patient justifiable. However, to reiterate, knowing the location of the roots in all planes of space is essential for quality orthodontic treatment at the beginning, during, and at the completion of such treatment. Knowledge of the root location is important for orienting the precision slots of orthodontic brackets to the crowns and roots of the teeth, the designing of force systems to move the teeth, the treatment progress and the final evaluation of the level of success of the treatment.

If proper orientation of the slot of an orthodontic bracket can be obtained in relationship to the long axis of the individual tooth, then for the rest of the treatment period the orthodontist has only to refer to the bracket slot to know where the root is located.

The present applicant, in U.S. Pat. No. 3,922,786, discloses a method and apparatus for forming and fitting orthodontic appliances. This method and apparatus came from the assumption that there is a correlation between the long axis of a tooth and its labial surface. Thus the contour of the backing of the orthodontic bracket would orient the slot to the long axis of the tooth. It is an assumption based on "averages" and is used by orthodontic manufacturers in producing current orthodontic brackets. They imply that placing a full sized arch wire in the precision bracket slots will render an ideal positioning of all tooth. E. L. Dellinger, in an article titled "A Scientific Assessment of the Straight Wire Appliance," American Journal of Orthodontics 73:290–299, 1978, contended that a full sized wire should not be used with an average inclination built into the bracket, otherwise the results may "be erratic, inconsistent and clinically unacceptable." However, practice with this device has indicated that although an "average" root axis angle can be determined by this apparatus and method, it is not sufficiently accurate in all situations. Furthermore, the method and apparatus works in reverse from actual placement of brackets on the patient's teeth. This becomes a very difficult procedure since it is more desirable to know of the root angles prior to bracket placement.

An indirect method for placement of brackets on a patient's teeth is indicated in U.S. Pat. No. 3,439,421 to T. E. Perkowski. Perkowski discloses an orthodontic articulator that permits reassembly of a patient's teeth into a desired form of realignment under an arch plate that is inscribed with a line indicating the arch configuration of the patient's dentition. A bracket positioning gauge is also disclosed for use in conjunction with the articulator for positioning brackets on an "ideal" model comprised of repositioned individual tooth models set-up under the arch plate in a wax base. Thus, individual adjustment of the tooth models is accomplished in the above mentioned manner, using heated spatulas, etc.

The Perkowski bracket placement mechanism involves the use of a base with a flat surface for sliding across a reference table surface. A bracket mounting arm is adjustably positioned on the sliding base with an extending pin positional by the adjustment mechanisms to the desired level at which the various brackets are to be placed on the "ideal set-up". The brackets are received by the pin along their arch wire slots. They will pivot about the axis of the pin as the pin is moved into position to attach the bracket to the model tooth. Therefore, orientation to the bracket slot is not controlled by the mounting arm but rather by the labial surface of the tooth and the bracket backing, which may vary considerably. The tooth curvature may cause the bracket to pivot on the carrying pin to a position wherein vertical wall of the slot is not perpendicular to the desired plane for the arch wire.

U.S. Pat. No. 3,521,355 to Pearlman discloses means for positioning orthodontic brackets. This mechanism is provided primarily for use in conjunction with plastic brackets and their use in the "direct" method of placement within the patient's mouth. The disclosure, however, does indicate the importance of positioning individual brackets in relation to the incisal surfaces of the individual teeth.

U.S. Pat. No. 3,657,817 to Kessling discloses a holder for orthodontic brackets used to provide a gripping surface by which an orthodontist or lab technician may hold individual brackets while they are attached as by spot welding to bracket bands. This patent again indicates the importance or accurate positioning for the brackets in relation to the associated teeth.

U.S. Pat. No. 3,521,354 to A. J. Stern et al discloses a method of assembling dowels in tooth dies. The purpose of the dowel arrangement is to facilitate insertion and removal of individual tooth models in relation to a cast base, without interfering with the dowel pins of adjacent tooth models. The purpose, therefore, is to arrange all the dowel pins in parallel orientation to one another, rather than to indicate the longitudinal root axis of the associated tooth to facilitate proper and accurate bracket placement.

It is valuable to view the individual tooth structure from mesial and distal aspects in order to determine root orientation. In direct placement of brackets on a solid set-up model or by the direct method on the patient's teeth, mesial and distal aspects are hidden by adjacent tooth structures. Therefore, the observer has ability only to view the features of a tooth from the labial, and with some difficulty the lingual aspects to determine root angulation. While this gives a general picture of the root orientation, it is not a precise method for locating the long root axes.

Of the above discussed disclosures, none provide means by which the long axes of the individual teeth may be accurately determined or indicated and recorded. Furthermore, substantial guess-work still remains in the placement procedures and adjustments by which bracket positioning is achieved. It therefore remains desirable to learn of and be able to record the exact location of roots of all the teeth in the mouth and, with such information available, obtaining the capability of accurately and effectively completing orthodontic treatment.

A first object of the present invention is to facilitate reproduction on the laboratory bench of all the crowns of the teeth of a patient's mouth with all the long tooth axes readily accessible.

Another object is to provide an apparatus system and process to initially locate the position of the roots and the manner of attachment in all planes of space that the roots have to their respective crowns.

It is a further object to record the spatial crown-to-root relationships by actually attaching a simulated root to the model of the crown of each tooth.

It is a still further object to make the precise location of any root initially and throughout treatment readily retrievable information by a simple index impression of the crowns which, of course, are visible in the mouth. The model crown with the simulated root attached is placed in the proper crown recess of the index impression. Plaster is poured around the simulated roots rendering a reproduction of the arrangement that the crowns have in the patient's mouth. By removing a little plaster on the labial side of the gum area adjacent to the root areas special features of the simulated root are exposed. These special features provide the needed information about the actual roots for or quality orthodontic treatment.

Another object is to provide an apparatus system by which individual crown models can be surveyed to determine precisely the exact orientation of the long tooth root axis in relation to the incisal, labial, lingual, mesial and distal surfaces of the crown.

A still further object is to provide an apparatus system by which a realistic "ideal" set up model of a patient's teeth can be produced, showing realistically the relative positions of the teeth following orthodontic treatment.

Another object is to provide an apparatus system by which the precision slots of orthodontic brackets can be positioned and recorded in relation to individual crown models of a patient's teeth.

A yet further object is to provide an apparatus and system for determining bracket thickness and backing caricature appropriate for individual crowns.

These and still further objects and advantages of the present invention will become apparent from the following description which, taken with the accompanying drawings, disclose a preferred form of the present invention.

BRIEF DESCRIPTION OF THE DRAWINGS

The present invention is illustrated in the accompanying drawings in which:

FIG. 1 is a diagrammatic view of a model made from a direct impression of a patient's teeth with an individual tooth crown highlighted therein;

FIG. 2 is an enlarged pictorial view of the highlighted crown model shown in FIG. 1;

FIG. 3 is a pictorial view of an individual crown model mounting disc;

FIG. 4 is a view of the disc with a crown model mounted thereon;

FIG. 5 is a pictorial view of a surveyor instrument;

FIG. 8 is an end view of the surveyor instrument as seen from the right in FIG. 6;

FIG. 9 is a fragmented pictorial view of a portion of the surveyor;

FIG. 10 is a pictorial view of a single dop rod;

FIG. 11 is a fragmented enlarged pictorial view showing an end of a special rod used for mounting simulated root sections in a root attachment plate;

FIG. 15 is a pictorial view of a grinding rack with a dop rod mounted thereon;

FIG. 16 is a pictorial view of a grinding rack adjustment plate;

FIG. 20 is a view showing the grinding rack mounted to the root attachment plate;

FIG. 21 is an enlarged detail showing the attachment of a finished tooth model to a dop rod;

FIG. 22 is a fragmented sectional view illustrating placement of a finished tooth model into an original impression taken from a patient's mouth;

FIG. 23 is a view of the resulting cast and tooth model taken from the impression shown in FIG. 22;

FIG. 24 is a pictorial view of a individual finished tooth model holder;

FIG. 25 is a somewhat enlarged side elevation view of the holder shown in FIG. 24 in relation to a tooth model and associated simulated root structure;

FIG. 29 is a pictorial view of the set-up articulator;

FIG. 30 is a pictorial view of an orthodontic placement instrument;

FIG. 31 is a pictorial view of a guide rod for the placement instrument shown in FIG. 30;

FIG. 32 is an enlarged side elevation view of a bracket selector device;

FIG. 33 is a plan view of the device shown in FIG. 32;

FIG. 34 is a fragmented detail view showing an alternate tip arrangement for the device illustrated in FIGS. 32 and 33;

FIG. 35 is an end view of the device as seen from the right in FIG. 32;

FIG. 36 is a fragmented view of a bracket placement device;

FIG. 37 is a view similar to FIG. 35 only showing an alternate form of the device for placement of brackets along the lingual surface of a tooth;

FIG. 38 is a pictorial view illustrating a precise line of placement along which a bracket is moved to be secured to an individual crown model.

DETAILED DESCRIPTION

The following, more detailed description of the present invention will be given in the order of the sequence of events as they occur in a process of orthodontic treatment. The apparatus involved will therefore be described as they come into use during the sequence of the steps involved.

An individual crown model is generally indicated at 10 in FIGS. 2 and 38 of the accompanying drawings. The crown model 10 was initially formed as an integral part of an original mal-occlusion cast 11 as seen in FIG. 1. The mal-occlusion cast 11 is formed from an impression 12 (FIG. 22) taken directly from the patient's mouth.

The crown models 10 actually represent only exact replicas of the visible portions of the patient's teeth. The actual teeth "T" (FIG. 39) include elongated roots "Rt" buried in alveolar tissues and are not visible. However, this area is of great concern in orthodontic treatment since movement of the crown "C" causes like movement of the root "Rt". Proper root dispersion in the alveolar tissues is critical to proper orthodontic treatment.

Figure 39:
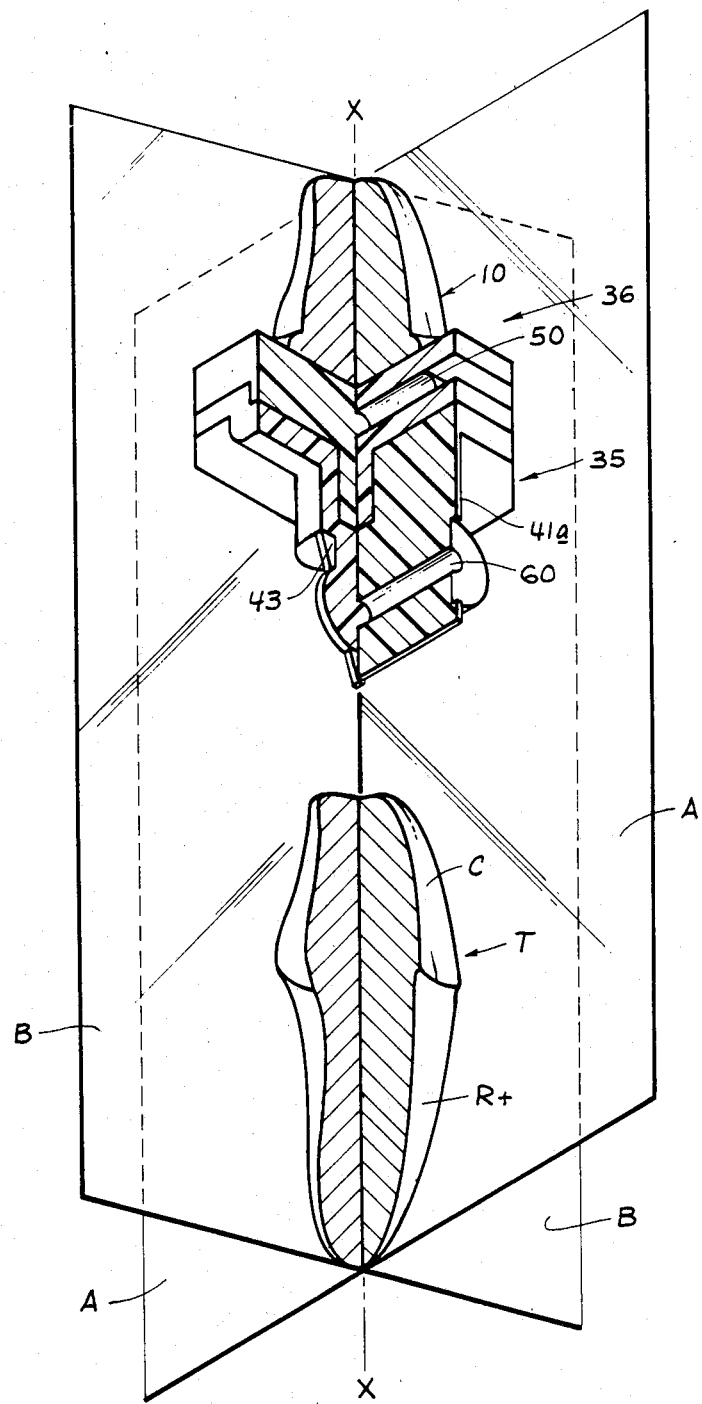
FIG. 39 is a diagrammatic view illustrating the relationship of an actual tooth, including crown and root, and a finished tooth model.

The present invention makes information available regarding the heretofore inaccessible long axis of the tooth labeled X—X in FIG. 39) which is normally hidden within the crown "C" and root "Rt". This information is then made use of by the present apparatus system to facilitate quality orthodontic diagnosis and treatment.

The particular crown model 10 is shown in FIG. 1 by solid lines while the remaining crowns in the mal-occlusion cast 11 are shown by dashed lines. The individual crown models are separated from the mal-occlusion cast 11 by sawing vertically through the cast material along side each crown. Impressions 12 may be taken of both upper and lower sets of the patient's teeth with a cast 11 being formed of each set. Unless described otherwise, the apparatus and process steps involved in the invention disclosed herein will function the same with either the upper or lower arch.

The crown model for purposes of later description, includes a crown section 14 and a gingival section 15. It is noted that the present system requires very little of the gingival section 15 to be cast. In fact, unlike other systems only the crown section 14 is needed. As a matter of practicality, however, sufficient gingival tissues are included in the impression to result in a cast model of the teeth in the appropriate dentition together in their original orientations.

Each of the crown sections 14 includes an incisal edge surface 16. This is the "chewing" surface of the tooth. The incisal edge 16 is at the extreme end of the lingual surface 17 and the labial surface 18. The lingual surface 17 is that surface facing a patient's tongue, while the labial surface faces outward against the cheek or lips.

Opposed sides of the crown section are designated the mesial side 19 and the distal side 20. The mesial side is situated toward the mid-line or center of the dental arch while the distal side is opposite, facing away the front mid-line or center of the arch. A mid-developmental ridge 21 may be found on the labial surface 18 of the crown section 14. This ridge, along with the other surfaces indicated above may be used in conjunction with the present apparatus and method for locating the precise angulation of the root section of the tooth that does not appear apparent from the model or from the actual tooth in the patient's mouth.

The original mal-occlusion cast 11 is formed from a wet plaster material and the resulting hardened cast includes a rough, uneven bottom surface. This base or bottom surface is indicated at 23, (FIGS. 1 & 2) for the individual tooth model 10.

Also, for purposes of later description, an orthodontic bracket 28 is shown in FIG. 38. This is a example of various forms of orthodontic brackets that are used in current practice and by no means represents a singular configuration or size. Generally, however, the bracket may be said to include a tooth engaging backing 31 that is curved along at least one plane to conform to the arched configuration of a complimentary tooth surface upon which the bracket is to be mounted. The bracket 28 includes a precision arch wire slot 32 that is precisely positioned along the bracket to receive a formed arch wire (not shown) that is used to distribute forces through the brackets to the attached patient's teeth. The precision arch wire slot 32 includes a vertical end wall 34 that is spaced by the bracket "thickness" from the tooth engaging backing 31.

Figure 12:
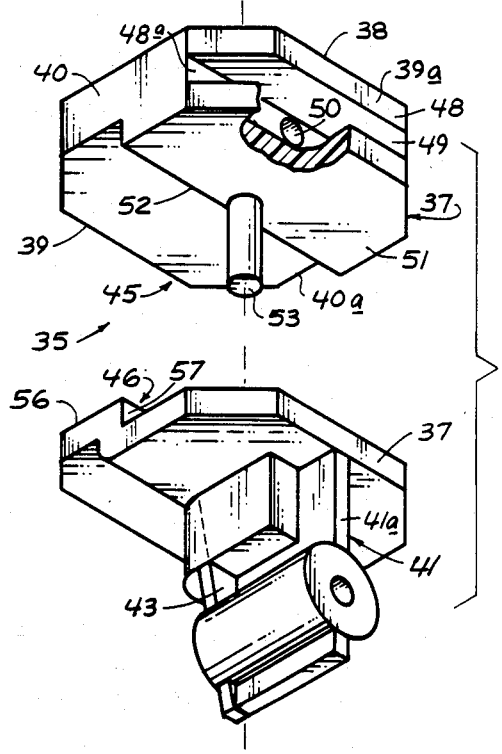
FIG. 12 is an enlarged pictorial view of a disassembled simulated root structure.
Figure 13:
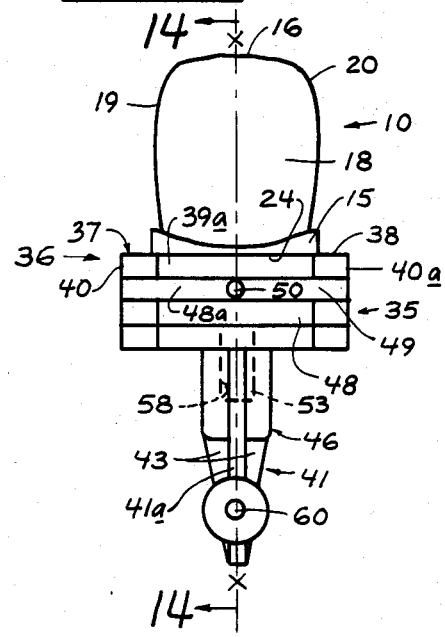
FIG. 13 is a frontal elevation view of a finished tooth model with attached simulated root structure in an assembled condition.
Figure 14:
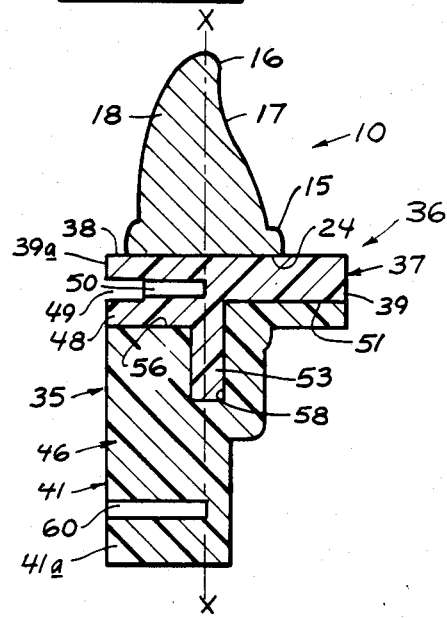
FIG. 14 is a sectional view taken substantially along line 14—14 in FIG. 13.

The present system and procedure involves use of simulated roots 35 (FIGS. 12-14) and attachment thereof to individual crown models 10 to produce a complete finished tooth model 36. The finished tooth models 36 accurately duplicate the actual crown-to-root configuration of the patients teeth (FIG. 39). Among other uses, information available from the tooth models 36 is invaluable to properly place and position brackets 28 to actual teeth. A simulated root 35 may be attached to each individual crown model 10 along a flat planar surface 24 (FIGS. 2, 13, 14, 18, 21) ground or otherwise formed along the base or bottom model surface 23. The flat planar surface 24 on the base of the crown model is oriented precisely perpendicular to the long root axis which is indicated in FIGS. 2, 13, 14 and 39 by the reference line X—X. The root axis (X—X) is normally not visible and is contained within the tooth crown and root. It is located as a line defined by the intersection of two planes. This relationship is diagrammatically shown in FIG. 39. One plane ("A") bisects the tooth lengthwise, passing through the tooth in a labial-lingual direction from the mid-developmental ridge 21. The other plane ("B") bisects the tooth lengthwise but passes through the tooth in a mesial-distal direction and equally divides the tooth thickness (between labial and lingual surfaces) at the gum line. The two planes A and B intersect and the line formed by the intersection is the long or root axis X—X of the tooth.

The planes A and B are accurately represented through features of the present simulated root to indicate the central long tooth axis X—X (from the labial-lingual and mesial-distal aspects) of a crown model 10 that has been properly mounted to the simulated root 35. Through proper attachment, the simulated roots 35 will accurately and consistently indicate this root orientation to facilitate proper initial and continuing orthodontic treatment of the patient's teeth.

An example simulated root 35 is shown in the drawings at FIGS. 12-14 and 39. Each simulated root 35 is basically comprised of a base plate 37 including a flat surface 38 for attachment to an associated crown model 10. This surface extends between opposed lingual and labial edges 39, 39a, and mesial and distal surfaces 40, 40a. The edges 39, 39a, and 40, 40a may extend beyond the tooth model initially, with excess to be trimmed off at a later stage.

Each simulated root 35 also includes a root fin member 41. Each fin member 41 includes a ridge or edge 41a in a plane perpendicular to the flat surface 38 to indicate the long axis X—X of a crown model 10 properly mounted to the flat surface 38. The ridge 41a is spaced labially from the mesial-distal plane B so it may be exposed and easily viewed when cast in a plaster base as shown in FIG. 23. The ridge 41a is bisected by plane A as shown in FIG. 39 and by its edges, indicates the mesial-distal angular orientation of the root axis X—X from the labial or lingual aspect. The surface of the ridge 41a is also parallel to plane B and may therefore indicate the labial-lingual angulation of the axis X—X. The fin member 41 is representative of the initial ⅔ of the roots length from the crown. It is this portion of the actual tooth root that runs true with the central root axis. The remaining ⅓ of the tooth root or apex, may taken any of various shapes and directions not at all indicative of the axis.

Web surfaces 43 are located on the fin, coplanar with plane B to indicate the labial-lingual angular orientation of axis X—X when viewed from the mesial or distal aspects. The web surface 43 is located on the fin member with a labial facing surface coplanar with the mesial-distal plane B. This surface will aid to indicate the labial-lingual angulation of the root axis X—X.

It is preferable that the simulated roots 35 be divisible along the base 37 into first and second sections 45, 46. Thus, the first section 45 includes the flat surface 38 for attachment to the corresponding flat surface 24 of a crown model 10. The second section 46 includes the fin member 41.

The first section 45 also includes a flat surface 48 extending along the labial edge 39a. The surface 48 includes a notch 49 formed therein that is perpendicular to the flat surface 48. The notch terminates at an upright wall 48a that is parallel to surface 48.

The wall 48a includes a hole 50 that extends into the first section. The hole terminates at a point along the root axis X—X. The depth of the hole 50, when probed with a wire, indicates the center of the simulated root at the particular level of the hole. The hole 50 is centered along the plane A so a wire probe may also indicate the rotation of the associated tooth in a mesial-distal direction as well as "torque" (angulation in labial-lingual direction).

A bottom surface 51 of the first section 45 faces opposite to the top flat surface 38. The bottom surface 51 may include a step 52 and an axially extending stem 53. The step and stem 52, 53 assure proper orientation of the two sections 45, 46 when joined together. They also facilitate means by which the two simulated root sections 45, 46 may be releasably held together.

The second section 46 includes a top platform surface 56 with a step 57 that matches the step 52 along the bottom surface of the first section. Thus, the steps 52 and 57 may be interfitted to properly align a crown model 10 on the flat surface 38 with the root fin member 41. The steps 52, 57 also mate along a plane parallel to the mesial-distal plane B to serve as further indication of the angular position of axis X—X (from the mesial or distal aspects). A hole or socket 58 extends axially into the second section 56 to releasably and frictionally mount the stem 53. The hole 58 is substantially coaxial with the long axis X—X. It is also situated approximately midway between the labial and lingual edges of the first section when the simulated root sections 45, 46 are assembled as a unit.

A hole 60 is provided adjacent the bottom end of the fin member 41. hole 60 is parallel to the hole 50 and is centered on plane A. It also ends at the axis X—X. A wire probe (not shown) can thus be inserted to indicate one point along the axis X—X. Two probe wires of equal length inserted to the ends of holes 50, 60 would therefore indicate by their exposed ends the precise orientation of the axis X—X in all planes of space.

The holes 50, 60 represent an important feature of the present invention. Orthodontists are greatly concerned about the "torque" (labial-lingual angulation) of the crowns and roots. Yet, until advent of the present invention, orthodontists had no way to assess teeth or models thereof to accurately determine this angle. Even X-rays lend no help in this area because this is a dimension in depth, thus not recordable with a two dimensional X-ray. The holes 50, 60 facilitate precise assessment of root angulation and so greatly assist the orthodontist in any area of treatment where it is useful to know the precise angulation of the root axis in all planes of space.

Additionally, the holes 50, 60 are located with openings on the labial side of the simulated root, spaced in the labial direction outward of the central axis X—X. The holes are therefore easily accessible even when the simulated roots are "poured up" in a case as shown in FIG. 23. In fact, the holes 50, 60 and root fin 41 being extended in a labial direction are relied upon when the finished models 36 are cast since they are the only readily accessible areas of the simulated roots 35. The other surfaces indicating axis position are buried in the plaster cast.

The individual crown models 10 must be individually positioned and the flat planar base or bottom surfaces 24 formed prior to mounting of the simulated roots 35 thereto. To this end, a crown surveyor 62 is provided which, along with a set of dop rods 82 and grinding rack 92, provide means for forming the flat bottom surface on the individual tooth models.

The crown surveyor 62 is shown in the drawings by FIGS. 5 through 9. A detail of a portion of the surveyor is shown in FIG. 9.

The crown surveyor 62 is utilized to angularly orient or releasably hold the individual crown models 10 in an aligned and centered position with the tooth axis X—X coaxial with a fixed axis Y—Y defined along the surveyor. To this end, each crown model 10 is releasably attached by a putty material 64 (FIG. 4) to a metal disc 63. This disc is about the size of a quarter and includes a small extension to serve as a handle. The crown model is placed on the disc with its incisal edge oriented outwardly and with the base or bottom surface 23 attached to the disc with a readily releasable material 64 such as putty. The surface of the crown model against the disc is the surface that the root of the tooth would normally be attached to and would emerge from.

The crown models are attached to discs 63 in the manner described and are placed, one at a time in the crown surveyor for crown-to-root alignment. The crown surveyor is operated to position the individual tooth models so the surface of the crown which in nature joins the root is at right angles to the tooth axis X—X and centered on the fixed axis Y—Y along the surveyor. When the bottom surface 23 of the crown is ground flat and at a right angle to the tooth axis X—X a simulated root 35 with its similar flat surface 38 can be attached to the crown to produce the finished tooth model 36 with the simulated root 35 precisely indicating the angular orientation of the long tooth axis X—X.

The disc 63 along with a crown model 10 is placed on a magnetic post 65 (FIG. 9) of an adjustable platform 67 of the crown surveyor 62. The adjustable platform 67 of the surveyor 62 includes two adjustment plates 68 and 70 that are spaced apart and pivot relative to one another about perpendicular axes. The plates are attached to a mechanism that facilitates centering of the crown model by means of a centering adjustment 72.

The post 65 is on the first plate 68. That plate 68 is mounted by a preferably vertical hinge member 69 to the second plate 70. The second plate 70 is mounted by a preferably horizontal hinge 71 to the centering adjustment 72. The axis for hinge 69 is perpendicular to that of hinge 71.

The centering adjustment includes a vertical adjustment knob 73 and a horizontal adjustment knob 74. The knobs 73 and 74 are connected to pinions that are directly rotated by the knobs to work against vertical and horizontal gear racks 75. These racks are mounted along appropriate horizontal and vertical ways 77. The horizontal way 77 is fixed to the frame for the crown conveyor surveyor 62. The vertical way is mounted by a gear housing 81 for movement along the fixed horizontal way. Thus, angular positioning may be achieved through the pivotal motion of plates 68 and 70 while vertical and horizontal motion of the entire adjustable platform assembly is accomplished through operation of the knobs 73, 74.

To facilitate proper alignment and positioning of a crown model 10 within the crown surveyor 62, first, top sight reference lines 78 (FIGS. 5 & 7) and second side sight reference lines 79 (FIGS. 5 & 6) are provided. These sight lines are secured to the frame of the crown surveyor on opposite sides of the crown model mounted within the surveyor. An incisal reference surface 80 of a fixed dop guide or groove 76 (FIGS. 5 & 8) is also used as one of the "sight lines". The groove 76 defines the fixed axis Y—Y with which the root axis X—X of the crown model is to be oriented coaxially. Lines 78 lie along a vertical plane intersecting axis Y—Y. Lines 79 lie along a horizontal plane intersecting axis Y—Y. These planes correspond with the planes A and B that intersect at the tooth axis X—X, and therefore assist the observer in properly aligning the crown model so the axes X—X and Y—Y coincide.

The crown model 10 is adjusted within the crown surveyor by the following process. Initially, the incisal view is observed, paralleling the incisal edge of the crown model along the incisal reference surface 80 of the dop guide groove 76. This adjustment is accomplished by turning the disc 63 on the post 65. The instrument will retain this alignment once the disc is so positioned on the magnetic post 65.

Next, the crown model is viewed from the labial aspect and the tilt platform is adjusted until the first top sight lines 78 are parallel to the crest of the mid-development ridge 21. This adjustment is accomplished by turning the first plate 68 that pivots about its a vertical hinge axis. This alignment is also retained on the instrument.

Next, the mesial surface 19 is viewed and is properly positioned in relation to the second side sight lines 79 by adjusting the remaining tilt platform 70. Both mesial and distal surfaces are considered during this procedure so both will be substantially oriented along the side sight llnes 79 with the lines (or planes represented by the lines) bisecting the crown model at the gum line and incisal edge.

Finally, the crown model is centered on the instrument by the vertical and horizontal adjusting knobs 73, 74. This is done viewing the crown model from the dop guide groove 76, substantially centering the crown model within the confines of the groove as indicated in FIG. 8. This procedure is used to position the crown model with its long axis X—X coaxial with the fixed axis Y—Y of the dop groove.

Figure 6:
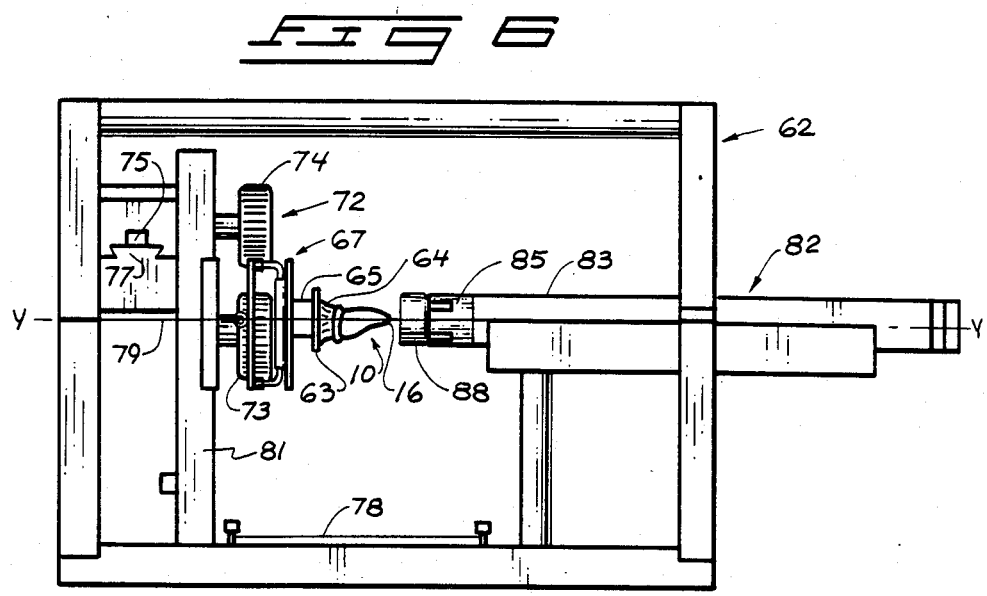
FIG. 6 is a side view of the instrument shown in FIG. 5 only with a dop rod and crown model shown mounted thereon.
Figure 7:
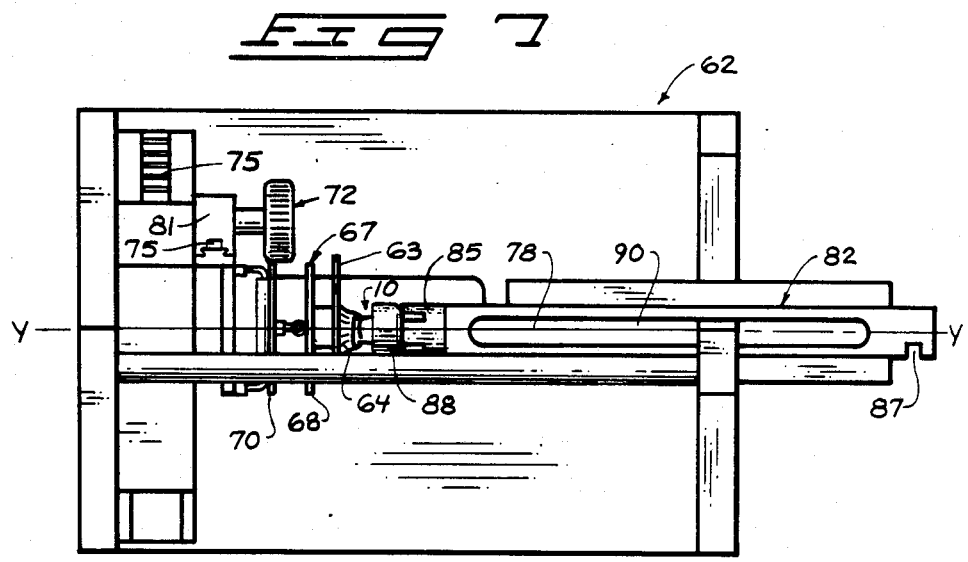
FIG. 7 is a top plan view of the instrument as shown in FIG. 6.

A dop rod 82 (FIG. 10) is slidably received within the dop guide and groove 76 with its central axis coaxial with the fixed axis Y—Y defined by the groove. It is elongated and preferably rectangular in cross section to match the configuration of the groove 76. It extends to an end 83 having an insulator 85. The insulator 85 includes a cup 88 that receives a crown model mounting dop material 84 (FIG. 21) that is shown in FIGS. 6 and 7. This material may be a form of adhesive or wax that will securely but releasably attach the crown model 10 to the dop rod with the long axis X—X coaxial with the central longitudinal axis of the dop rod.

An opposite end 86 of the dop rod 82 may include a lateral groove 87. This groove 87 may be used to elevationally position the dop rods in a later procedure.

Each dop rod 82 is also provided with an indented area 90. This area may releasably receive note labels (not shown) that can be used for indicating particular information regarding to the particular crown model mounted to the dop rod.

It is noted that an individual dop rod 82 is provided for each of the individual crown models 10. Thus several such rods will be used in typical orthodontic procedures.

If dop wax is used in the cup 88 as a mounting material 84, the wax is first heated before the dop rod is placed in the groove 76. The rod with the heated, pliable wax, is then moved axially in the groove 76 toward the positioned crown model until the incisal edge 16 of the crown model touches the mounting material 84 and becomes imbedded to the full depth of the cup 88 (FIGS. 7 and 21). The dop rod 82 is allowed to remain in this position until the dopping wax cools and hardens around the crown model. The wax thus attaches the crown model firmly to the dop rod.

The dop rod can then be removed from the surveyor 62, pulling the crown model free of the softer mounting material 64 on the metal disc 63. The crown is now precisely positioned along the dop rod with the base or bottom model surface 23 facing outwardly, and with the long tooth axis X—X coaxial with the longitudinal dop rod axis.

Figure 17:
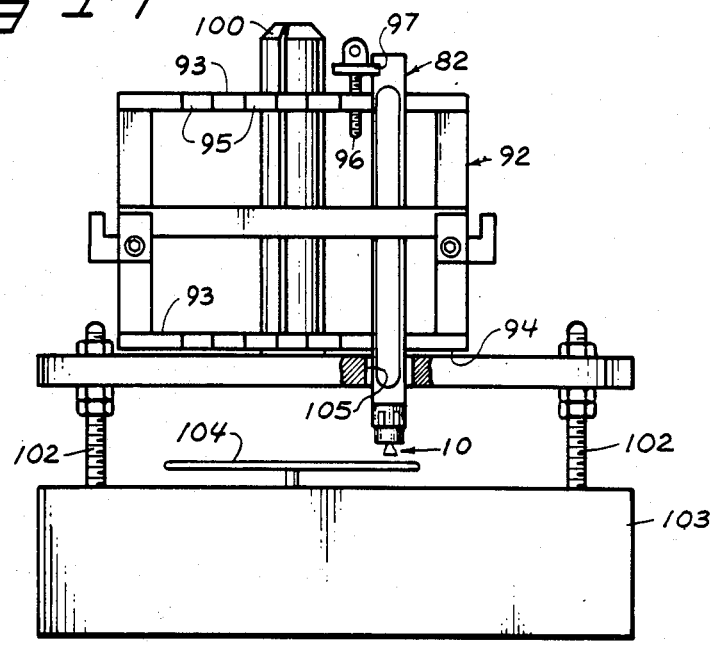
FIG. 17 is a view of the grinding rack and an associated grinding rack adjustment plate mounted to a conventional grinding machine.
Figure 18:
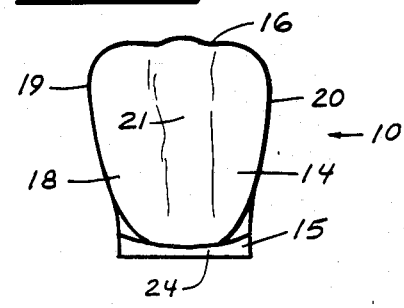
FIG. 18 is a view of a crown model following the grinding operation performed by the machine shown in FIG. 16.

The dop rod will maintain the orientation of the positioned crown model so the flat ground surface 24 (FIG. 18) can be formed thereon at right angles to the rod and in a plane perpendicular to the long root axis X—X of the crown model. This is accomplished by use of a grinding rack 92 (FIGS. 15, 17, 19) that as briefly discussed above, is also part of means for forming the flat ground surface 24 along each crown model 10.

It is noted at this point that the procedure outlined above for properly aligning individual crown models in the crown surveyor is performed for each crown model taken from original mal-occlusion casts 11, including both upper and lower arches. There is a possible 32 teeth involved. However, a typical orthodontic case will usually involve 22 to possibly 26 individual teeth.

The dop rods 82 with individual crown models 10 secured thereto, are mounted to a grinding rack 92. The grinding rack 92 is a device that holds the dop rods, sixteen at a time, in upright positions and at right angles to parallel vertically spaced grinding rack plates 93. Each rod 82 is received in a complementary recess 95 formed in each of the spaced plates 93.

The rods are arranged in pairs as are the crowns involved. That is, there are two centrals, two laterals, two cuspids, etc. Therefore, the paired crown models are arranged in the grinding rack next to one another with the dop rod groove 87 facing one another. The paired grooves 87 each receive an adjusting plate 97 (FIG. 15) that is adjustably positioned on the top plate 93 by an adjusting screw 96. Screws 96 can be turned to adjust the height of the engaged dop rods to control the level of the surfaces to be formed along the base or bottom surfaces 23 of the models. This level should be selected to be just gingivally of the gum line on the labial surface of each tooth model. The thickness of the gingival section 15 should be approximately one half millimeter.

The vertically spaced plates 93 of the grinding rack include coaxial keyed holes 98 formed along an axis that is precisely parallel to the axes of the dop rods and crown models held thereon. These keyed holes 98 slidably receive a spindle 100 (FIGS. 16, 17) having a keyway extending along its upright length. The keyed spindle 100 is mounted perpendicularly to a grinding rack adjustment plate 101. The grinding rack adjustment plate 101 is a device that is mountable over a horizontal flat grinding surface 104 (FIG. 17) of a conventional grinding machine 103. Holes 105 are formed through the plate to allow the dop rods 82 to pass through. The adjustment plate 101 is attached to the grinding machine by means of height adjusting supports 102. These supports 102 may be selectively adjusted to assure a perpendicular orientation between the spindle 100 and the flat grinding surface 104.

The grinding rack 101 with rods and crown models attached, is placed on the spindle 100 with the keyed holes 98 being fitted over the spindle. The rack is thus guided by the spindle 100 in the precise perpendicular orientation of the spindle in relation to the flat grinding surface 104. The grinding rack will slide down the spindle until the attached crown models projecting below the bottom grinding rack plate 93 extend through the holes 105 and touch the grinding surface 104. As the grinding surface 104 moves, the base or bottom surfaces 23 of the individual crown models are formed by the grinding surface 104. A flat surface 24 that is at a precise perpendicular relationship to the long axis X—X of each crown model is thus produced on each model. The grinding continues until a stop surface 94 of the bottom plate 93 of the grinding rack rests on the grinding rack adjustment plate 101. At that point, all crown models on the ends of the dop rods 82 will have a precise flat ground surface 24 formed thereon, ready to mount a simulated root 35.

Figure 19:
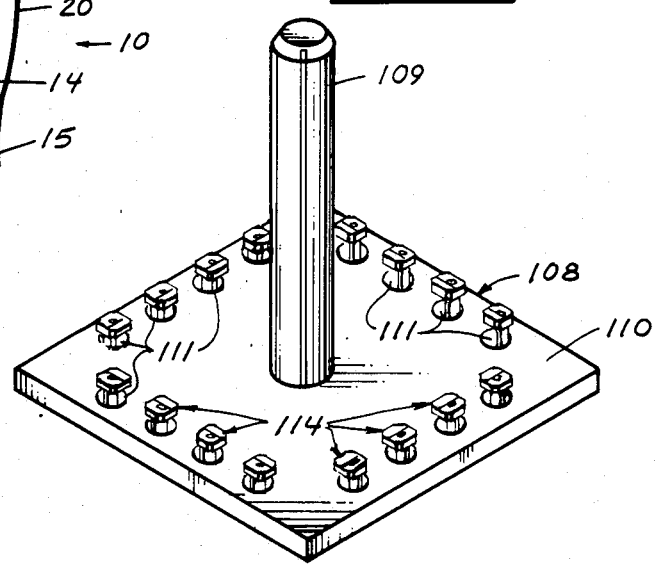
FIG. 19 is a pictorial view of a root attachment plate.
Figure 26:
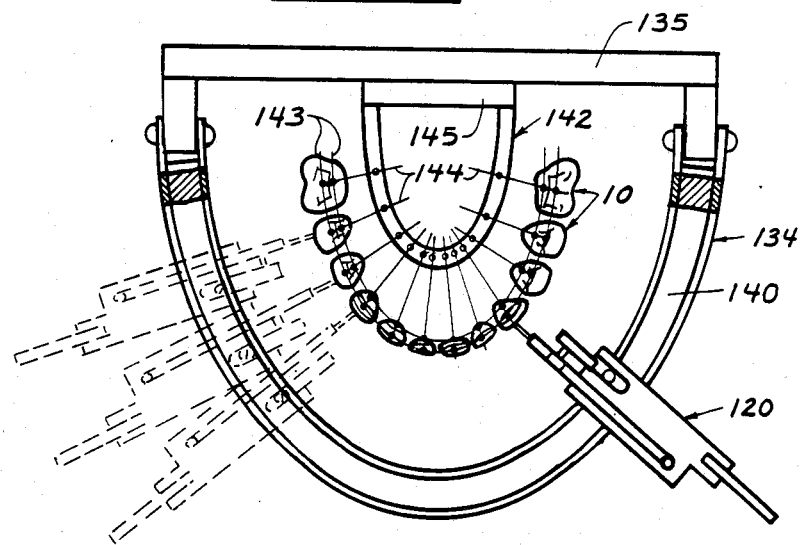
FIG. 26 is a plan view of a set-up articulator with a tooth model holder mounted thereto.
Figure 27:
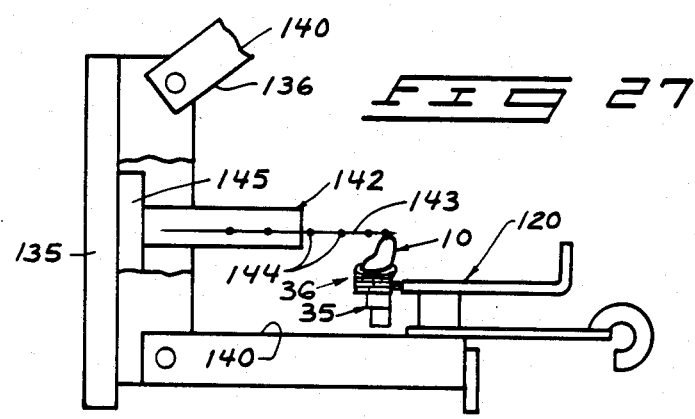
FIG. 27 is a side elevation view of the set-up articulator shown in FIG. 26 only with a portion of a top arch bar broken away.
Figure 28:
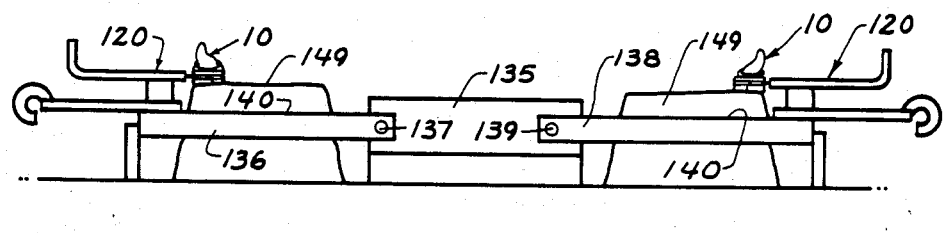
FIG. 28 is a reduced view of the set-up articulator folded flat on the table surface.

The grinding rack 92 and attached dop rods with the crown models having presently ground surfaces 24 on each, is next placed on a root attachment plate 108 (FIGS. 19, 20). The root attachment plate 108 is somewhat similar in design to the grinding rack adjustment plate 101. It includes an upright spindle 109 that includes an axial key slot slidably received through the keyed holes 98 of the grinding rack. The root attachment plate also includes a horizontal surface 110 that is precisely perpendicualr to the spindle 109. A number of recesses 111 are provided about the surface, one for each dop rod. These recesses are in direct vertical alignment with the dop rods held on the grinding rack 92 when positioned on the spindle 109.

Within each of the recesses 111 is a root receiver section 114 (identical to second root sections 46) held securely in position by rigid cast material 113 within the individual recess.

The root receiver sections 114 are positioned initially in the molding material 113 by means of the root placement of mounting devices 89 (FIG. 11). These devices 89 are used to mount and hold first root sections 45 in prescribed precise orientations with the surfaces 48 facing outwardly when attached to the grinding rack. A series of the devices 89 with attached root receiver sections 114 and second sections 46 releasably mounted thereto are secured to the grinding rack and lowered along the spindle 109 until the root members 41 of the second sections 46 become immersed in wet cast material held in the recesses 111. The grinding rack is allowed to rest in this position while the cast material hardens about the submerged portions of the receiver sections 114. The grinding rack is removed after the material has hardened. The mounting devices 89 will pull away from the receiver sections 114, leaving them in precise positions along the horizontal surface 110. These permanently fixed receiver sections 114 are thus in position to be used to secure other first root sections 45 to the individual crown models.

The root attachment plate is used firstly by inserting a number of first root sections 45 in the permanently attached receiver sections 114 along the horizontal root attachment surface 110. The upwardly exposed flat surfaces 38 of the positioned first sections, therefore, face the downwardly oriented flat surfaces 24 of the crown models 10. These two surfaces are maintained by the root attachment plate precisely parallel with one another. Adhesive may be placed on one or both of the aligned surfaces. The grinding rack can then be lowered to bring the surfaces 24 and 38 into direct abutment. The adhesive will permanently secure the first root sections 45 to the abutting individual crown models 10.

After the adhesive has dried, the rack can be lifted to pull the first root sections clear of the permanent receiver sections 114. The permanent receiver sections 114 are thus left in position along the plate to receive a subsequent set of first root sections 45 and a subsequent set crown models 10.

The crown models 10 and attached root sections 45 may be taken from the dop rods 82. Another set of second root sections 46 can then be attached to the first sections 45 that are now secured to the crown models 10. This completes the finished tooth model 36 of the patient's tooth with an accurately attached simulated root that exists in the same relationship in all planes of space that the actual root would have to the associated crown. Edges of the flat base portions of the root may now be trimmed toward the crown (FIG. 23).

The individual finished tooth models 36 may now be inserted back into the original impression 12 (FIG. 22). Each crown 10 of the finished tooth models model 36 will be received in a matching recess within the impression. The crown areas will thus be covered by the mating impression material, as well as portions of the gingival tissue section 15. The impression is then poured up in plaster. When the plaster solidifies, the original impression can be removed. The individual crown models 10 are thereby releasably anchored by the simulated roots 35 in the cast base 118. Part of the cast base 118 can then be ground away to expose the holes 50 and 60 and the ridges 41a of root fins 41 (FIG. 23).

This completes the process by which the patient's teeth are reproduced in an orthodontic cast base 118 with the holes 50 and 60 and the root fin ridges 41a exposed to indicate actual root angulation of the teeth in the patient's mouth. This is very useful to the orthodontist who can now properly visualize the tooth in its original mal-occluded position and, in addition, determine exactly where the root exists in the alveolar tissues below the exposed crown surface of the tooth. The simulated root 35 can be probed, using the holes 50 and 60 to indicate the exact position of the long axis for the root and the angular orentation of the tooth crown with respect to the root axis.

Knowing the long axis of the mal-occluded teeth helps in planning the force systems needed to make the desired tooth movements necessary to correct the patient's mal-occlusion. This information is also extremely helpful to the orthodontist in bracket placement. Further, the crown-root relationship shown may function as an effective research tool to indicate precisely the changes in angulation of tooth roots over a treatment period by the use of progressive cast models. A succession of such models would also show the orthodontist how treatment is progressing and if, at the end of treatment, all teeth concerned have been properly realigned. Other benefits and valuable information beyond the few mentioned above will become more apparent as the system is use.

Further apparatus and process steps may be involved from this point onward to facilitate accurate placement of brackets on the various tooth models.

Each finished tooth model 36 of the mal-occlusion is placed on an individual tooth holder 120 (FIGS. 24 & 25). The individual tooth holders 120 are instruments that hold the finished tooth models firmly. They function as model positioning means for adjustably mounting the simulated root 35 and attached crown model 10 along a reference plane in relation to the indicated root axis X—X.

Each tooth holder 120 includes a projection rod 121 that accurately fits into the notch 49 and hole 50 of a first root section 45. The projection provides a firm hold on the root section and attached crown model 10.

The projection 121 is rotably mounted (on a horizontal axis) within a sleeve 112. Sleeve 122, in turn, is mounted by a pivot 123 (on an axis perpendicular to that of sleeve 122) to a height adjustment 124. A screw 125 can be turned, operating the height adjustment 124 to raise or lower the projection rod 121 in relation to a pedestal 126. Guides 127 are situated on opposite sides of the screw to elevationally guide the adjustment 124 up and downwardly as the screw 125 is turned. It is noted that the elevational adjustment may be made without changing or effecting the positions of rod 121 or pivot 123.

The pedestal 126 is mounted to a flat base 128. A reference plane surface 129 is situated along a bottom side of the flat base 128. The reference surface 129 is used to indicate a flat reference plane for selective positioning of a finished tooth model 36 attached thereto.

The projection 121 is adjustable in two directions about its axis as defined by the sleeve 122. The axis at pivot 123 is substantially perpendicular to the projection axis. Thus, an attached finished tooth model 36 can be selectively positioned at any desired location about the two axes.

When the individual tooth holders are first mounted to the finished tooth models 36 in the mal-occlusion cast base 118, adjustment is made to orient the reference plane surfaces 129 parallel to the flat bottom surface of the cast base or to a visualized occlusal plane. In practice the casts are typically formed with flat bottom surfaces that are substantially parallel to the occlusal plane. Therefore, it is easier to orient the flat base 129 of the tooth holders visually with the flat bottom surface of the cast base 118.

The individual tooth holders 120 have the unique ability to transfer the individual finished tooth models 36 from the original mal-occlusion with the original mal-position of the individual teeth maintained. That is, the individual finished tooth models 36 can be set up away from the cast base 118 substantially in this same orientation in which they existed when held in position on the base 118.

This is preferably accomplished through use of a set-up articulator shown generally at 134 (FIGS. 26–29). The set-up articulator 134 is provided as means having a planar set-up surface 140 thereon corresponding to the reference plane of the cast base 118 and reference surfaces 129 of the individual tooth holders 120. The reference plane is provided as as a magnetic surface to receive and hold the individual tooth holders 120. The attached finished tooth models 36 can then be positioned by the individual tooth holders 120 from original mal-occlusion positions thereof to corrected positions.

The set-up articulator 134 may include a rigid back plate 135 pivotably mounting a top arch bar 136 at pivots 137, and a bottom arch bar 138 at pivots 139. Each of the bars 136, 138 define a planar magnetic surface 140 upon which the individual tooth holders 120 are to be received. The bars 136 and 138 are each formed in a semi-circlular arch to approximate the general shape of a dental arch. The bars may be positioned with one over the other in a manner similar to dental arches. In this position, (FIG. 29), the bars exist at a spacing of approximately 1½ inches and are parallel to one another. The pivots 137 and 139, however, allow the bars to be spread apart away from each other and the back plate 135 placed horizontally (FIG. 28) such that both planar surfaces 140 face upwardly.

An adjustable arch form indicator 142 is releasably mountable to the back plate 135. The adjustable arch form indicator includes at least one but preferably two arch form indicator wires 143 mounted thereon. These wires extend outwardly from a base 145 that may be magnetically attached to the set-up articulator back plate 135. Adjustable holders 144 extend between the base 145 and indicator wires 143. If two wires 143 are utilized, it is preferred that they be spaced apart by a distance of approximately 3 mm. This allows the tips of the cusps of the various teeth to be at slightly diffent heights in the set-up of the tooth models. Such as, the lower cuspids incisal cusp tip is always high (½-1 mm) than the adjacent lateral tooth.

The arch form wires may be adjusted by the holders 144. Holders 144 slide moved in or outwardly in relation to the base 145 to orient the wires 143 in coincidence with the patient's lower arch. This is done by using the mal-occlusion cast base 118 of the lower arch with attached finished tooth models 36. This step is accomplished prior to removal of the individual finished tooth models 36 from the cast base to the set-up articulator 134. After the wires have been formed, the arch form indicator is placed on the back plate 135 of the set-up articulator. This is done with the back plate upright and perpendicular to the magnetic surface 140 of arch bars 138. The upper bar 136 is pivoted to a position substantially parallel with the back plate and out of the way to facilitate the following set-up procedures.

The individual tooth holders 120 now can be attached to the individual tooth models of the lower arch via the attached simulated root sections 45 and removed from the cast base 118.

This is done by inserting the projecting pins 121 of the holders into the holes 50 of the first simulated root section 45. The bases 128 of the holders are pivoted by means of sleeves 122 and pivots 123 to bring the flat reference surfaces 129 into parallel orientation with the occlusal plane, or flat bottom surface of the cast 118. The holders are then removed from the models. The crown models 10 and attached sections 45 are pulled from the case base 118, leaving the second root sections 46 in place on the base. The crown models and attached root sections 45 are then re-attached to the associated holders by re-inserting the now properly positioned pins 121 into the holes 50.

It is noted that the second simulated root sections 46 will remain in the case base 118. Therefore, another set of second sections 46 may be mounted to reconstruct the finished tooth models 36. The tooth models 36 may now be transferred to the set-up articulator 134.

The individual tooth models 36 will be held in their original positions by the holders 120 with the flat bottom reference surfaces 129 of the bases 128 co-planar along the magnetic surface 140 on the articulator 134. The complete mal-occlusion with tooth models are suspended by the tooth holders 120 on the magnetic bar 138 with the same angulation that the crowns had in the mal-occlusion. Set up of the arch is assisted by the arch form indicator wires 143 that are situated slightly above the tooth models. The wires indicate, by the space between them, where the incisal edges of the individual tooth models should be located. Thus, the tooth models 36 have been transferred from the mal-occlusion to the set-up articulator maintaining their original planes of space. That is, the tooth models and simulated roots maintain the same angulations in the labial-lingual direction and the mesial-distal direction that existed in the mal-occlusion.

The individual tooth holders 120 are designed so the tooth models can be moved in vertical (up and down) direction by the adjustments 124 without altering or changing the labial-lingual or mesial-distal angulations. These angulations can be changed to a realistic "ideal set-up" later by the projection and pivot arrangements of the individual tooth holders when so desired.

An ideal set-up can be arranged using the adjustale tooth holders 120 after the entire arch has been set-up on the articulator. It is initiated starting at the lower mid-line (point between the two lower central incisors). The two lower centrals are moved, using the attached projection rods 121 and pivots 123 to the anticipated finished treatment position. This is done using the arch indicator wires to establish the height for the incisal edge of each tooth and the correct rotational position thereof. Next, the lower laterals are positioned, followed by the cuspids, and so forth. The height and rotation of each tooth model is determined by the arch form indicator. The desired angulation of each tooth is determined by the long axis X—X (labial aspect) of the crown and root. This information is readily available from the simulated rods 35.

Once the lower tooth models have been positioned in their anticipated completion of orthodontic treatment positions, the arch form indicator is removed. At this time, the tooth models of the upper arch may be transferred to the top arch bar 136 just as the lowers were previously transferred. That is, the individual tooth holders are positioned in the tooth model and attached first root sections 45 of the models set-up in an upper mal-occlusion arch. The tooth models and attached sections 45 are then carried to the upper arch bar 136 on the associated tooth holders 120. The original second sections 46 of the simulated roots will stay in the upper mal-occlusion cast base for the upper arch of the patient and a second set of second sections 46 are placed on the now free first sections 45 to again complete the simulated root structures.

The upper centrals are first placed on the top arch bar 136. Their height and rotational position is determined by the previously positioned lower tooth models. This is done by periodically pivoting the upper arch bar 136 into its horizontal orientation, bringing the upper tooth models into close proximity with the previously placed lower models. The mesial-distal and labial-lingual angulations are determined by viewing the attached simulated roots. The root fins 41 readily provide the needed information. This is because the long axis of each tooth model and root is visible—not covered by gum tissue.

The upper "setup" is started by placing the upper central incisors on the top arch bar 136 and establishing their correct position as stated above. After the upper centrals have been correctly positioned and checked with the arch bars in parallel positions, the upper bar 136 is again raised and the upper laterals are placed on the top arch bar 136. The upper bar is again lowered to its parallel position and the upper laterals are positioned in relation to the lower tooth models that have already been positioned. These models are then again checked and adjusted via the attached holders 120 if necessary. This procedure is continued until all of the upper tooth models have been located in their anticipated completion of orthodontic treatment positions. Therefore, by having an arch form determined from the original mal-occlusion; by having visible long axes of all of the crowns and roots; and by having readily and completely adjustable individual tooth holders to position each tooth, ideal set-up of the upper and lower tooth models can be produced which should be obtainable in a realistic sense with orthodontic treatment starting from the original mal-occlusion.

Each finished tooth model 36 is held by the associated tooth holder 120 to allow rapid positioning of each tooth model with extreme accuracy.

The capability provided by the individual tooth holders 120 in positioning each tooth model in the set-up articulator 134 as it was in the mal-occlusion is of significance. This is due to the fact that to move teeth in certain directions is very limited in orthodontic treatment. Thus, in moving the teeth to the anticipated complete orthodontic treatment position, one must evaluate if such movement is possible orthodontically, based on where the tooth is positioned originally. A meaningful set-up of teeth is a reality with the present system and process.

This system allows for initial determination of the directions that the roots emerge from the crowns. It records the direction of root attachment to the crown by actually indicating along the simulated root the actual root position as it is in the patient's gum and alveolar tissues. The present simulated root indicates the long axis of the root to allow viewing of such axis in order to determine the anticipated completion of orthodontic treatment positions of the associated tooth.

The unique manner of holding the tooth model from the labial aspect while positioning via the associated holders 120 is also worthy of note. In other known indirect orthodontic methods, the crown model must be held from the gingival area while the technician or orthodontist attempts to position the crown. This method of holding the crown obstructs the area where the root of the crown is actually located. One must then guess where the roots are located in such an arrangement.

With the present system and process, the long axes of the roots are fully visible. Further, the labially or outwardly oriented tooth holders 120 are situated outward of the tooth models 10 and attached simulated roots 35. This places the adjustment mechanisms of the tooth holders 120 in a greater arc than the model teeth themselves. This gives room to manipulate the adjustment mechanisms of each tooth holder 120 to achieve visible and realistic positioning of the associated tooth models.

The ideal setups of tooth models held in the set-up articulator are retained by fixing the second simulated root sections 46 of the ideal setups ideal set-up cast models 149. Thse may be formed from soft plaster held in shallow containers positioned on the table within the arch bars 136 so the soft plaster will encompass the second sections of each simulated root. When the plaster hardens, the individual tooth holders may be removed, producing each ideal set-up cast model 149 in a rigid plaster base.

The lower ideal set-up cast model 149 is then positioned in an orthodontic bracket placement instrument 151. The orthodontic bracket placement instrument functions, in part, as a cast support means having a cast support table 153 thereon and an arch shaped platform 157. The table 153 and platform 157 are movable relative to one another such that the cast and tooth models thereon can be located precisely in relation to the platform. The instrument 151 is used to facilitate accurate placement of orthodontic brackets 28 on the tooth models which have been positioned in the ideal set-up cast model 149 in their anticipated completion of orthodontic treatment positions. With this instrument 151, orthodontic brackets can accurately be placed on the labial or lingual surfaces of the tooth models in the "ideal set-up" dental arch. This is true of both upper and lower arches.

The plate 153 is adjustable in height in all planes. This is facilitated by height adjusting screws 158 extending between the table 153 and a fixed base 159. The platform 157 is secured to the base 159 by upstanding legs 161.

Upright studs 163 (FIG. 36) are provided on the table 153. These studs are used to receive and "key" the ideal set-up cast 149 which may be mounted thereto by wet plaster 156. The plaster 156 will adhere to the cast 149 and form around the studs 163 and attach the ideal set-up model cast 149 to the plate 153 so it may be removed and returned to the plate in a precisely oriented position. Thus, the ideal set-up cast 149 can be removed and returned again to the same position.

The platform 157 is adjacent to the adjustable table 153. It is semicircular in shape and is preferably fixed by the legs 161. The table 153 may be spaced approximately one half inch away from the platform 157. The table 153 has a curved outer edge surface complementary to the inside curvature of the platform.

The platform 157 may be approximately two inches wide with a flat planar top surface. It also includes a slot 162 that is semicircular in the same configuration of the platform. The slot 162 is utilized to hold guide rods 167 of a bracket orienting and placement means to be described further below.

The ideal set-up model is positioned one at a time on the orthodontic bracket placement instrument 151 by first positioning the wet plaster base 156 firmly over the studs 163 on the plate 153. The ideal set-up model is then placed on top of the wet plaster. The set-up cast model is oriented such that the labial surfaces of the associated crown models 10 face outwardly and in approximately alignment with the arched edge of the table 153. The plate is then adjusted up or downwardly by the screws 158 to determine the desired height for placement of orthodontic brackets along the crown models.

This is done by utilizing a bracket indictor means 175 (FIG. 32-35) along the flat surface of the platform 157. The bracket indicator means 175 may include a slide bar 176 that includes a flat surface slidably recieved on the platform 157. One end of the slide bar 176 includes a projecting pin indicator 177. The pin indicator is pointed at its outward end and spaced by the slide bar 176 a short distance above the flat platform 157. The pin indicator 177 is therefore held in a relatively fixed plane as determined by the surface of the platform 157.

The height adjustment screws 158 are turned to raise or lower the ideal set-up model 149 in relation to the platform 157 and projecting pin indicator 177. The adjustments are made until the pin indicator will touch the labial surface of each crown model in the ideal set-up model 149 at a position thereon that will accept or mount an orthodontic bracket. This level exists in a plane that intersects all the crown models in the ideal set-up.

Height adjustment is accomplished by adjusting the screws 158 and checking the points along the labial surfaces of the crown models 10 with the pin indicator on both sides in the molar area and toward the front in the central area. When the adjustment is complete, the orthodontist or technician is assured that brackets can be attached to all the desired crown models in a common plane. This plane is the effective height at which brackets will be attached through further procedures described below.

Guide means, in the form of a number of guide rods 167 (FIG. 31) are mounted to the platform 157. The guide rods 167 are used to define precise lines relating to each crown model along which a bracket is centered and attached to a tooth. These lines pass through each crown model along the labial surface thereof at a point labeled "R" and the lingual surface labeled "R'" (FIGS. 32, 33, 36–38). Elevation of these points R, R' has previously been set by adjustment of the table 153 in relation to the platform 157.

The individual guide rods 167 are each rectangular in cross section and elongated to slidably mount a bracket indicator means 175 (described below) along the surface of the platform 157. The guide rods 167 may be selectively held in position on the platform by downward projecting threaded shafts 168 securely affixed thereto. The shafts 168 are loosely received through the platform slot. Thumb screws 169 are threadably engaged with the shafts 168 and can be turned to pull the guide rods firmly against the platform surface and secure them in any angle along the surface in relation to the associated tooth models.

The bracket selection indicator means 175 may be utilized to position a guide rod 167 properly for each of the crown models 10 in the ideal set-up model 149. This is done again using the projecting pin indicator 177 and, in addition, an incisal edge reference rod 178 mounted at an end of the slide bar.

The slide bar 176 is slotted at 180 along its bottom surface to slidably receive a guide rod 167. The slide bar 176 may be positioned over a guide rod 167 to orient the guide bar length along a prescribed line relating specifically to the individual crown models.

To selectively position the guide rods 167, a bracket selector device 175 is placed successively over each guide rod and is moved roughly into position along the labial surface of a selected crown model. The pointed end of the projecting pin indicator 177 is then moved into engagement with the crest of the mid-developmental ridge 21 along the subject crown model 10. The slide bar 176 and guide rod 167 carried in the slot 180 is then slidably adjusted angularly along the platform surface while maintaining contact at the mid-developmental ridge of the model. The slide bar is thus pivoted at the point of the indicator during this movement. The object is to align the incisal edge reference rod 178 parallel to the incisal edge line of the crown model. The reference rod 178 is oriented perpendicularly to the slide bar and projecting pin indicator and so will orient the guide rod 167 perpendicularly to the incisal edge.

The R and R' points are established by the above procedure along the line passing through the model, indicating the approximate center point for attachment of an orthodontic bracket 28. Actually, the R, R' points are located along lines that are situated in the plane determined by the height adjustment earlier stated. Further, each is centered mesial-distally by the projecting pin indicator touching the mid-developmental ridge.

Once properly positioned, the guide rods 167 are secured in place by simply tightening the thumbscrews 169. The guide rods are thus held in position and lend repeatability to the various following procedures involved with placement of individual brackets on the tooth models.

Another feature of the bracket selector device 175 is adjustment means on the slide bar that is used to indicate the thickness dimension of each tooth (labial-lingual) at the bracket height on the tooth. These distances are commonly to as "ins and outs".

The in and out distance is basically the distance from the crown surface (labial or lingual) receiving the bracket to a line perpendicular to the appropriate incisal edge of the tooth. Brackets currently in use are supplied in "average" thickness differences to compensate for the various thicknesses of teeth. However, there is variation in tooth thickness in nature from one tooth to another and again a variation in one person from another. The thickness of teeth radically varies at the height or level of measurement. In addition, the angulation of the tooth in a labial-lingual direction alters the above thickness measurement.

The adjustment referred to above will give an accurate reading to the orthodontist or technician for selection of a proper bracket thickness. The correct thicknesses of the brackets are such that the bracket slots 32 form a smooth, common arch configuration that will readily accept an orthodontic arch wire with the wire fitting flush against each of the inner vertical wall surfaces 34 of each bracket 28 without requiring adjustment on the ideal set-up.

The in-out adjustment means is a component of the bracket indicator means 175 and includes a movable indicator 182 attached to the upper surface of the slide bar 176. The indicator will slide axially along the length of the bar. It includes a forward end 183 that may be selectively positioned over the incisal edges of the crown models. A market 184 on the indicator rearward of the forward end 183 includes another pointer that is situated adjacent to a scale 185 secured to the slide bar. The scale 185 includes appropriate indexed indicia measuring from a zero reference point. The "zero point" is the point at which the forward indicator end 183 and the point of the projecting pin indicator 177 are in exact vertical alignment. The indicia incremented from the zero point can therefore indicate the thickness dimension of the crown model from the "R" point to the incisal edge of the associated crown model. This thickness dimension can be taken in consideration when selecting brackets of various thickness dimensions to allow for "ins and outs". It is noted this adjustment may function equally as well for determining ins and outs for upper as well as lower teeth. For uppers, a straight indicator end 183 may be used. For lowers, an end 186 (FIG. 34) having a slight "dog leg" can be used to indicate the appropriate incisal edge surface of the lowers without requiring adjustment of the scale 185.

It is very desirable to approach a flush engagement between the bracket backing 31 and the directly adjacent tooth configuration. Therefore, the bracket indicator means 175 includes a contour measuring device 190 for use in conjunction with the previously determined R, R' points. The contour measuring device 190 will provide a meaningful indicator of the contours of the surface of the crown where the orthodontic bracket will be placed. Therefore, the orthodontic bracket selected for placement on the tooth will have a backing 31 of similar contours to allow close approximation of the two surfaces, namely the backing of the bracket and the crown surface.

To this end, a series of feelers 191 are positioned about the central projecting pin indicator 177. The feelers 191 are axially slidable on an end plate 193 of the slide bar 176 and are spring biased to extend parallel to the projecting pin indicator 177 to engage the curved surface of the associated crown. This is all accomplished with the projecting pin indicator 177 being in contact with the "R" point established earlier. There may be six of the feelers in two groups of three. Three short feelers 191 may be located on a horizontal plane above the indicator 177 and three longer feelers 191 below. The center feelers in each group of three are on a vertical line with the indicator pin 177.

On the top surface of the end plate 193 is a measuring scale 192 (FIG. 33) that is situated below the top feelers 191. The scale can be formed such that the rearward ends the top three feelers will be visible with the scale positioned between the two horizontal groups. The rearward ends of the feelers will be automatically positioned adjacent appropriated indicia along the scale once the outer ends engage the associated tooth surface. The lower set of longer feeles 191 may have rearward ends that extend rearwardly beyond the rearward ends of upper set. Another scale 194 is used in association with the lower feelers 191. This scale 194 can be formed with appropriate indexed indica on a transparent "window" such that the lower feeler ends can be viewed from above and so their postions with repsect to the scale indicia can be recorded.

Appropriate provisions (not shown) can be made along the slider bar 176 to position the feelers in an opposite facing direction in order to indicate curvature on the lingual surfaces of crown model. This provision could simply be an appropriate inverted "U" shaped end plate for mounting the feelers and pin indicator 177 along the inside of the ideal set-up arch, with the pin indicator touching the R' point.

A value may be established for each point touched by a feeler 191, with the center "R" having a zero value. The measurements indicated by the various feelers 191, can therefore indicate curvature of the associated tooth surface in both mesial-distal directions and incisal-gingival directions. This data can be used to select an appropriate curvature of an existing bracket backing 31, or to determine the curvature needed to be imposed by bending or otherwise forming an appropriate bracket backing 31.

It may be understood from the above that the bracket indicator means 175 when used properly will precisely indicate the exact thickness of bracket required to maintain a particular arch conformity and the curvature of the bracket backing required for relatively flush engagement with the surfaces of the patient's teeth.

Once the above indicated measurements have been taken and the guide rods 167 have been properly positioned, a bracket placement slider 195 (FIGS. 36, 37) may be utilized to attach the various brackets 28 to the individual crown models 10. Each slider 195 includes a slide bar 196 that is slotted to slidably receive the guide rod 167. A bracket slider 195 is provided for each of the guide rods and will slide back and forth over the flat surface of the platform 157 in the path defined by the previously positioned guide rods 167. A forward or leading end of each bracket slider 195 rigidly mounts a projecting mount 197. The bracket mount 197 includes an edge surface that conforms intimately to the bracket arch wire slots 32. The mount is elevationally located at the precise elevation of the projecting pin indicator 177 of the bracket indicator means 175. Thus, if the bracket slider were moved to engage the adjacent crown model, the bracket mount 197 would touch the crown surface at the R point. In fact, the R would be exactly centered on the bracket mount 197. Thus, a bracket positioned on the bracket mount 197 may be moved by the slider into a precisely centered orientation with the center point of the vertical slot wall 34 precisely positioned along the line passing through the R, R' points.

With lingual brackets 28a, (FIG. 37), the projecting bracket mount 197 will assume a substantially inverted U shped configuration. The bracket mount in this configuration is substantially identical to that described above.

Adjustable stops 198 (FIG. 36) are provided at outward ends of the slider bars 196. The stops 198 are selectively adjustable to position the ends of the bracket mounts 197 in relation to the adjacent crown model surfaces by distances determined by the "ins and outs" measurements indicated above.

The stops 198 may be positoned by use of an appropriate feeler gauge (not shown) inserted between the adjacent crown model surface and bracket mount 197 prior to placincg an orthodontic bracket 28 on the end. The feeler gauge thickness is selected by a calculation based from a measurement taken by the bracket indicated means 175 in conjuncton with the dimension relating to the surface of the "thickest" tooth of the arch (usually one of the canines), and the "thinnest" bracket (measured from backing 31 to vertical slot wall 34).

For example, say a bracket of 1 mm thickness is to be used on a cuspid ("thickest tooth") measuring (via movable indicator 182) 4 mm. This establishes a common distance of 5 mm (4 mm+1 mm) from the incisal edge (arch) to the vertical slot wall 34 of each bracket placement on the ideal set-up model 149. Thus, if the thickness measurement for a adjacent lateral tooth model is 2 mm, the required bracket thickness would be 5 mm minus 2 mm equals 3 mm. A 3 mm feeler gauge is thus selected and placed with one surface on the "R" (or R') point of the lateral model. The slider bar 196 is then moved along the associated guide rod 167 until the bracket mount 197 abuts the other side of the 3 mm feeler gauge. The stop adjustment 198 is then set so the slider will always stop at this point.

A bracket having a 3 mm thickness is then selected which also has the appropriate curvature determined by feelers 191, if one is available. If not, sufficient additional cement of filler (not shown) is placed on the bracket backing to fill the gap between the crown model and bracket backing. The filler then becomes the bracket backing when the bracket (and attached filler) is removed from the model for placement on the patient's actual tooth.

The individual brackets are attached to the tooth models by placing a drop of adhesive-filler along the bracket backings. The brackets are then slid forwardly by the bracket sliders 195 until the backings come into contact with the appropriate surfaces of the tooth models. The slider is then left to hold the brackets in position while the adhesive-filler dries.

It is preferred that a releasable adhesive be used between the brackets and crown models so the brackets may be later removed for actual attachment to the patient's teeth. The removed brackets may be replaced by a new set of brackets or appropriate simulated brackets (not shown) that can be used for other purposes during the correctional period. The guide rods 167 and the adjustable stops 198, being previously set, aid in this procedure, which otherwise is a repetition of the above described process for attaching the brackets 28 or 28a. This will be discussed later in more detail.

After all the brackets have been attached to the tooth models in the ideal set-up, the crown models and attached first root sections 45 are removed from the ideal set-up and again positioned with the associated root sections 45 fitted to sections 46 waiting in the mal-occlusion cast base 118. This is the orientation the brackets will actually be in when mounted to the patient's teeth.

The brackets can now be removed from the crown models and placed on the patient's teeth, using known conventional practices. The material used to transfer the brackets from the crown models to the teeth must be of a solid nature, such as dental compound so as to secure and control the position of the precision slot 32 of the bracket, approximating the bracket backing and the crown surfaces. This procedure does not allow abutment of the bracket backing and the crown surface to influence the precision slot angulation. The angulation or orientation of the precision slot to the crown and root is establishd by the fixed edge surface of the bracket mount 197 fitting intimately into the precision slot 32 of the orthodontic bracket. Adhesive is placed on the backing of the bracket before mounting to the patient's teeth. The brackets are then placed against the identical teeth in the patient's mouth. The bracket backings plus the adhesive-filler will conform to the crown surfaces and the brackets to the corresponding tooth surfaces.

After the brackets have been placed on the teeth, the orthodontist designs and fabricates arch wires to move the teeth. Initially these arch wires are of small diameters and are "tied-in" to the bracket slots, thus applying moment and forces to the crowns and roots of the teeth. The arch wires will tend to line-up the slots on the brackets on the teeth, one to each other. Thus, it becomes apparent why bracket placement (actually proper slot orientation to the crown and roots) is the most important part of orthodontic treatment.

Inaccurately placed brackets produce mal-positioned teeth. Heavier or larger diameter arch wires are placed as the bracket slots align. Eventually, full size arch wires (rectangular in cross-section) that intimately fit into the bracket slot can be placed and produce ideal results if the bracket slots were oriented proper to the crowns and roots and so attached to the crowns.

Traditionally, the orthodontist constructs and fabricates the arch wires at the dental chair by measuring directly from the patient's mouth and marking the arch wire to indicate where bends should be made in the arch wire. Theses procedures require the orthodontist to continually estimate rotations of the crowns and roots, elevation and intrusion of the crowns and roots, angulations, mesial-distal and labial-lingual of the crown and roots. From these observations, the orthodontist may design force systems to improve the tooth positions.

Archwires are fabricated and "tied" to the individual teeth. The patient is usually checked every 2–6 weeks by the orthodontist who from memory and notes written from previously appointment attempts to evaluate the changes that occurred. How much have the teeth moved from their previous positions? The previous position is not the original mal-occlusion position but rather a constant changing position, visit by visit.

With the present system, as mentioned earlier, a second set of brackets or simple precision slots can be placed on the crown models just as they have been placed on the teeth in the mouth. Simple index impressions of the occlusal surfaces of the crowns of the teeth in the mouth can be made periodically, the tooth models 36 inserted, and plaster casts made to show progress of treatment and to assist in arch wire fabrication. Thus, it is easy to reproduce on the lab bench not only the crown arrangement but more importantly, all the long axes of all the teeth at any time during treatment.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. An orthodontic model root structure for mounting a cast crown model including an upper crown section extending from an incisal edge along labial and lingual surfaces to a lower gingival section and terminating at a base surface oriented at a selected angle to the long axis of the crown model and for visually indicating the long axis of the crown model, the orthodontic model root structure comprising:
    a base plate having a base plate surface including spaced labial and lingual edges for mounting the crown model with the base surface of the crown model in flush abutment against the base plate surface and with the labial and lingual edges of the base plate adjacent corresponding labial and lingual surfaces of the crown model; and
    fin means on the base plate extending therefrom opposite the base plate surface for visibly indicating a long central axis;
    wherein the base plate is oriented relative to the fin means such that a crown model may be mounted to the base plate with the long axis thereof coaxial with the long central axis indicated by the fin means.

2. The orthodontic model root structure as claimed by claim 1 wherein the base plate includes first and second root sections, with the base plate surface on the first root section and the fin means on the second root section; and
    wherein the first and second root sections are releasably connectable.

3. The orthodontic model root structure as claimed by claim 2 wherein one of the root sections includes a stem projecting outward therefrom and the remaining root section includes a socket for receiving the stem of the one root section.

4. The orthodontic model root structure as claimed by claim 3 wherein the stem and socket are situated coaxially and perpendicular to the surface of the base plate.

5. The orthodontic model root structure as claimed by claim 1 wherein the base plate includes a hole extending into the base plate and terminating at the long central axis.

6. The orthodontic model root structure as claimed by claim 5 wherein the fin means includes a fin ridge and a hole extending inwardly from the fin ridge; and
wherein the hole in the base plate and the hole in the fin member terminate along the long central axis thereof which may be coincidental with the long axis of a crown model when the crown model is mounted to the base plate surface.

7. The orthodontic model root structure as claimed by claim 1 wherein the base plate and fin means are releasably mounted together and include mating steps to assure proper alignment of the base plate and fin means to the long axis of a crown model mounted on the base plate surface.

8. An orthodontic model root structure for mounting a crown model outside a patient's mouth in such a manner that the long axis of the tooth from which the crown model was made is visibly indicated in relation to the crown model; the orthodontic model root structure comprising:
an elongated fin member;
first means on the fin member for indicating the angular orientation of a first plane passing through the fin member;
second means on the fin member for indicating the angular orientation of a second plane intersecting the first plane along a line; and
a base plate mounted to the elongated fin member and having a base plate surface thereon adapted to receive and mount the crown model with the long axis thereof extending along the line of intersection of the first and second planes.

9. The orthodontic model root structure as claimed by claim 8 wherein the base plate is comprised of:
a first root secton including the base plate surface; and
a second root section releasably engageable with the first root section and including the fin member.

10. The orthodontic model root structure as claimed by claim 9 further comprising means between the first and second root sections for securing the first and second root sections in a prescribed orientation relative to one another.

11. The orthodontic model root structure of claim 35 wherein the means between the first and second root sections includes a stem projecting outward from one of the root sections;
a mating socket formed in the remaining root section for releasably receiving the stem; and
mating steps formed in the first and second root sections to orient the sections in a prescribed angular relationship about the line of intersection.

12. The orthodontic model root structure of claim 10 wherein the base plate surface is substantially flat in a plane perpendicular to the stem and wherein the stem is coaxial with the line of intersection of the two planes indicated by the first and second means.

13. The orthodontic model root structure of claim 8 wherein the base plate surface includes a flat plane surface for mounting the crown model and wherein the flat plane surface is perpendicular to the line of intersection of the two planes indicated by the first and second means.

14. The orthodontic model root structure of claim 8, including a labial surface thereon and wherein the first means includes at least one hole extending from an open end along the labial surface into the simulated root structure along an axis within the first plane and terminating at the line of intersection of the first and second planes.

15. The orthodontic model root structure of claim 14 wherein the second means includes a surface on the simulated root structure coplanar with the second plane.

16. The orthodontic model root structure of claim 8 wherein the first means includes a ridge formed along the fin member and extending from the base plate, the ridge having at least one edge thereof oriented to visibly indicate a mesial-distal angular orientation of the first plane.

17. The orthodontic model root structure of claim 16 wherein the ridge is parallel to the second plane to indicate a labial-lingual angular orientation thereof.

18. The orthodontic model root structure of claim 16 wherein the base plate surface includes mesial, distal, labial and lingual edges and wherein the ridge is situated adjacent the labial edge.

* * * * *